United States Patent [19]

Brown

[11] Patent Number: 4,743,954
[45] Date of Patent: May 10, 1988

[54] INTEGRATED CIRCUIT FOR A CHEMICAL-SELECTIVE SENSOR WITH VOLTAGE OUTPUT

[75] Inventor: Richard B. Brown, Salt Lake City, Utah

[73] Assignee: University of Utah, Salt Lake City, Utah

[21] Appl. No.: 742,721

[22] Filed: Jun. 7, 1985

[51] Int. Cl.⁴ .............................................. H01L 27/04
[52] U.S. Cl. ...................................... 357/25; 357/41; 357/48
[58] Field of Search .................. 357/25, 40, 23.15, 41, 357/45, 48

[56] References Cited

U.S. PATENT DOCUMENTS

| | | | |
|---|---|---|---|
| 4,020,830 | 5/1977 | Johnson et al. | 128/2 E |
| 4,133,735 | 1/1979 | Afromowitz et al. | 357/25 |
| 4,332,658 | 6/1982 | Tsuboshima | 357/25 |
| 4,385,274 | 5/1983 | Shimada et al. | 357/25 |
| 4,411,741 | 10/1983 | Janata | 204/1 T |
| 4,437,969 | 3/1984 | Covington et al. | 357/25 |
| 4,508,613 | 4/1985 | Busta et al. | 357/25 |

OTHER PUBLICATIONS

Lauks et al, IEEE International Conf. on Solid State Sensors and Actuators, (Jun. 10, 1985), pp. 122–124.
Ammann et al., "Neutral Carrier Based Hydrogen Ion Selective Microelectrode for Extra- and Intracellular Studies," Analytical Chemistry, vol. 53, pp. 2267–2269.
Bergveld, P., "Development of an Ion-Sensitive Solid-State Device for Neuro-Physiological Measurements," I.E.E.E. Transactions on Bio-Medical Engineering, vol. BME-17, pp. 70–71, Jan. 1970.
Bergveld, P., "Development, Operation, and Application of the Ion-Sensitive Field-Effect Transistor as a Tool for Electrophysiology," I.E.E.E. Transactions on Biomedical Engineering, Vo. BME-19, pp. 342–351, Sep. 1972.
Bergveld, P., "The Operation of an ISFET as an Electronic Device," Sensors and Actuators, vol. 1, pp. 17–29, Mar. 1981.
Bergveld, P., "Design Considerations for an ISFET Multiplexer and Amplifier," Sensors and Actuators 5 (1984), pp. 13–20.
Blackburn, G. F., Molecular Adsorption Measurement with Chemically Sensitive Field Effect Transistors, Ph.D. Dissertation, University of Utah, Dec. 1983, p. 50.
Blackburn et al., "Field-Effect Transistor Sensitive to Dipolar Molecules," Applied Physics Letters, vol. 43, pp. 700–701, Oct. 1983.
Buck, R. P., "Kinetics and Drift of Gate Voltages for Electrolyte-Bathed Chemically Sensitive Semiconductor Devices," I.E.E.E. Transactions on Electron Devices, vol. ED-29, pp. 108–115, Jan. 1982.

(Continued on next page.)

Primary Examiner—William D. Larkins
Attorney, Agent, or Firm—Workman, Nydegger & Jensen

[57] ABSTRACT

An integrated circuit for a miniaturized solid-state chemical sensor. The integrated circuit includes a chemical-selective membrane which provides an electric signal in response to contact with a particular chemical or group of chemicals in a fluid. The chemical-selective membrane is attached to the integrated circuit by a membrane definition layer. An electrically conductive layer beneath the membrane definition layer provides electrical contact between the chemical-selective membrane and one of the input transistors of the voltage-follower amplifier. The chemical-selective membrane is formed separately from the gate of the input transistors and is designed as a integrated input to the amplifier. The output of the chemical sensor is a low impedance electric signal represented as a voltage which corresponds to the chemical activity present at the chemical-selective membrane/fluid interface. In one embodiment, multiple chemical sensors are fabricated on a single integrated circuit wherein each chemical-selective sensor forms an integrated input to a separate amplifier. Included on the integrated circuit of that embodiment is circuitry to allow for multiplexing of the outputs of the amplifiers to one or both of two output pads provided on the integrated circuit.

28 Claims, 17 Drawing Sheets

OTHER PUBLICATIONS

Cheung et al., "Theory, Fabrication, Testing, and Chemical Response of Ion-Sensitive Field-Effect Transistor Devices," in Theory, Design and Bio-Medical Applications of Solid State Chemical Sensors, Cleveland, Ohio: CRC Press, 1978, pp. 92, 103-106, 115.

Compte et al., "A Field Effect Transistor as a Solid-State Reference Electrode," Analytica Chimica Acta, vol. 101, pp. 247-252, Nov. 1978.

Durst, R. A., "Potential Pitfalls in the Use of Ion-Selective Electrode-Reference Electrode Pairs," in Theory, Design and Biomedical Applications of Solid State Chemical Sensors, Cleveland, Ohio: CRC Press, 1978, p. 158.

Esashi et al., "Integrated Micro Multi Ion Sensor Using Field Effect of Semiconductor," I.E.E.E. Transactions on Biomedical Engineering, vol. BME-25, pp. 184-192, Mar. 1978.

Fjeldly et al., "Solid-State Ion-Selective Electrodes with Integrated Electronics," J. Electrochem. Soc: Electrochemical Science and Technology, vol. 126, pp. 793-795, May 1979.

Fjeldly et al., "Fluoride Electrodes with Reversible Solid-State Contacts," J. Electrochem. Soc: Electrochemical Science and Technology (Jun. 1980), pp. 1299-1303.

Frank et al., "Partial Least Squares Solution for Multicomponent Analysis," Analytical Chemistry, vol. 55, pp. 1800-1804, Sep. 1983.

Fricke, G. H., "Ion-Selective Electrodes," Analytical Chemistry, vol. 52, pp. 259R-275R, Apr. 1980.

Gaarenstroom et al., "Computer-Controlled Interference Correction for Ion-Selective Electrode Measurements in a Flowing System," Analytical Chemistry, vol. 50, pp. 811-817, May 1978.

Haemmerli, A. M., Study of Dynamic Characteristics of Ion Selective Field Effect Transistors, Ph.D. Dissertation, University of Utah, Jun. 1982, p. 75.

Haemmerli et al., "Equilibrium Noise in Ion Selective Field Effect Transistors," Journal of the Electrochemical Society, vol. 129, pp. 2306-2312, Oct. 1982.

Haggin, J., "Faster, Smaller Integrated Sensors in Offing for Process Control," C&EN (Jun. 4, 1984), pp. 7-13.

Harame et al., "An Implantable Ion Sensor Transducer," IEEE International Electron Device Meeting Technical Digest, Washington, D.C.: IEEE, 1981, p. 467.

Ho et al., "Encapsulation of Polymeric Membrane-Based Ion-Selective Field Effect Transistors," Sensors and Actuators, vol. 4, pp. 413-421, Nov. 1983.

Huber et al., Solid State Chemical Sensors, New York: Academic Press, 1985, pp. 65-162.

Janata, J., "An Immunoelectrode," Journal of The American Chemical Society, vol. 97, pp. 2914-2916, May 1975.

Janata et al., "Chemically Sensitive Field-Effect Transistor to Detect Organophosphorus Compounds and Pesticides," Aviation, Space, and Environmental Medicine, vo. 52, pp. 666-671, Nov. 1981.

Janata et al., "Chemically Sensitive Field Effect Transistors," in Ion-Selective Electrodes in Analytical Chemistry, vol. 2, H. Freiser, Ed., New York: Plenum Press, 1980, pp. 109, 124, 139, 147, 168-169.

Jochum et al., "Error Propagation and Optimal Performance in Multicomponent Analysis," Analytical Chemistry, vol. 53, pp. 85-92, Jan. 1981.

Janata et al., "Thermodynamics of Chemically Sensitive Field Effect Transistors," in Theory, Design and Biomedical Applications of Solid State Chemical Sensors, Cleveland, Ohio: CRC Press, 1978, pp. 42-46.

Kelly, R. G., "Microelectronic Approaches to Solid State Ion Selective Electrodes," Electrochimica Acta, vol. 22, pp. 1-8, Jan. 1977.

Ko et al., "Multiple ISFET with Integrated Circuits," Sensors and Actuators, vol. 4, pp. 496-500, Jun. 1984.

Kowalski, B. R., "Intelligent Instruments of the Future," in International Union of Food Science and Technology Proceedings from the Food Research and Data Analysis Symposium, Sep. 1982.

Lundstrom et al., "A Hydrogen-Sensitive MOS Field-Effect Transistor," Applied Physics Letters, vol. 26, pp. 55-57, Jan. 1975.

Matsuo et al., "Methods of ISFET Fabrication," Sensors and Actuators, vol. 4, pp. 496-500, Jun. 1984.

McBride et al., "Ion-Selective Field Effect Transistors with Polymeric Membranes," Analytica Chimica Acta, vol. 101, pp. 239-245, Nov. 1978.

(List continued on next page.)

OTHER PUBLICATIONS

McKinley et al., "In Vivo Continuous Monitoring of K+ in Animals Using ISFETs," Journal of Medical Instrumentation, vol. 24, pp. 93–97, Feb. 1980.

McKinley et al., "In Vivo Continuous Monitoring of Ionized Calcium in Dogs Using Ion Sensitive Field Effect Transistors," Critical Care Medicine, vol. 9, pp. 333–339, Apr. 1981.

Moss et al., "Potassium Ion-Sensitive Field Effect Transistor," Analytical Chemistry, vol. 47, pp. 2238–2243, Nov. 1975.

Moran et al., "Analysis with Ion Selective Electrodes Using the Generalized Standard Addition Method," submitted to Analytical Chemistry, Department of Chemistry, University of Washington.

Oesch et al., "Field Effect Transistors Sensitive to Sodium and Ammonium Ions," Analytical Chemistry, vol. 53, pp. 1983–1986, Nov. 1981.

Poteat et al., "Transition Metal-Gate MOS Gaseous Detectors," I.E.E.E. Transactions on Electron Devices, vol. ED-29, pp. 123–129, Jan. 1982.

Rechnitz, G. A., "Bioselective Membrane Electrode Probes," Science, vol. 214, pp. 287–291, Oct. 1981.

Saxberg et al., "Generalized Standard Addition Method," Analytical Chemistry, vol. 51, pp. 1031–1038, Jun. 1979.

Senderowicz et al., "High Performance NMOS Operational Amplifier," in Analog MOS Integrated Circuits, P. R. Gray, D. A. Hodges, and R. W. Brodersen, Eds., New York: I.E.E.E. Press, 1980, pp. 56–62.

Sibbald, A., "A Chemical-Sensitive Integrated-Circuit: The Operational Transducer," to be published in Sensors and Actuators, Electrochemistry Research Laboratories, University of Newcastle upon Tyne.

Sibbald et al., "A Miniature Flow-Through Cell with a Four-Function ChemFET Integrated Circuit for Simultaneous Measurements of Potassium, Hydrogen, Calcium and Sodium Ions," Analytica Chimica Acta, vol. 159, pp. 47–62, May 1984.

Sibbald et al., "On-Line Patient-Monitoring System for the Simultaneous Analysis of Blood $K^+$, $CA^{2+}$, $Na^+$ and pH Using a Quadruple-Function ChemFET Integrated-Circuit Sensor," Medical and Biological Engineering & Computing, vol. 23, pp. 329–338, 1985.

Smith, R. L., Ion-Sensitive Field Effect Transistors with Polysilicon Gates, Ph.D. Dissertation, University of Utah, 1982.

Smith et al., "Transient Phenomena in Ion Sensitive Field Effect Transistors," Journal of the Electrochemical Society, vol. 127, pp. 1599–1603, Jul. 1980.

Wong et al., "The Potential Uses of Solid State Chemical Sensors in Patient Monitoring During Anesthesia," in Theory, Design and Biomedical Applications of Solid State Chemical Sensors, Cleveland, Ohio: CRC Press, 1978, p. 263.

Yee et al., "Ion-Selective Implantable Electrodes Fabricated by Hybrid Technology," Theory, Design, and Biomedical Applications of Solid State Chemical Sensors, Cleveland, Ohio: CRC Press, 1978, pp. 81–89.

Kalivas et al., "Compensation for Drift and Interferences in Multicomponent Analysis", Analytical Chemistry, vol. 54, pp. 560–565, Mar. 1983.

(MASK LAYOUT 9)
Ⓜ RICHARD BLAINE BROWN (MASK LAYOUT 8)
Ⓜ RICHARD BLAINE BROWN (MASK LAYOUT I)
Ⓜ RICHARD BLAINE BROWN (MASK LAYOUT 2)
Ⓜ RICHARD BLAINE BROWN (MASK LAYOUT 3)
Ⓜ RICHARD BLAINE BROWN (MASK LAYOUT 4)
Ⓜ RICHARD BLAINE BROWN

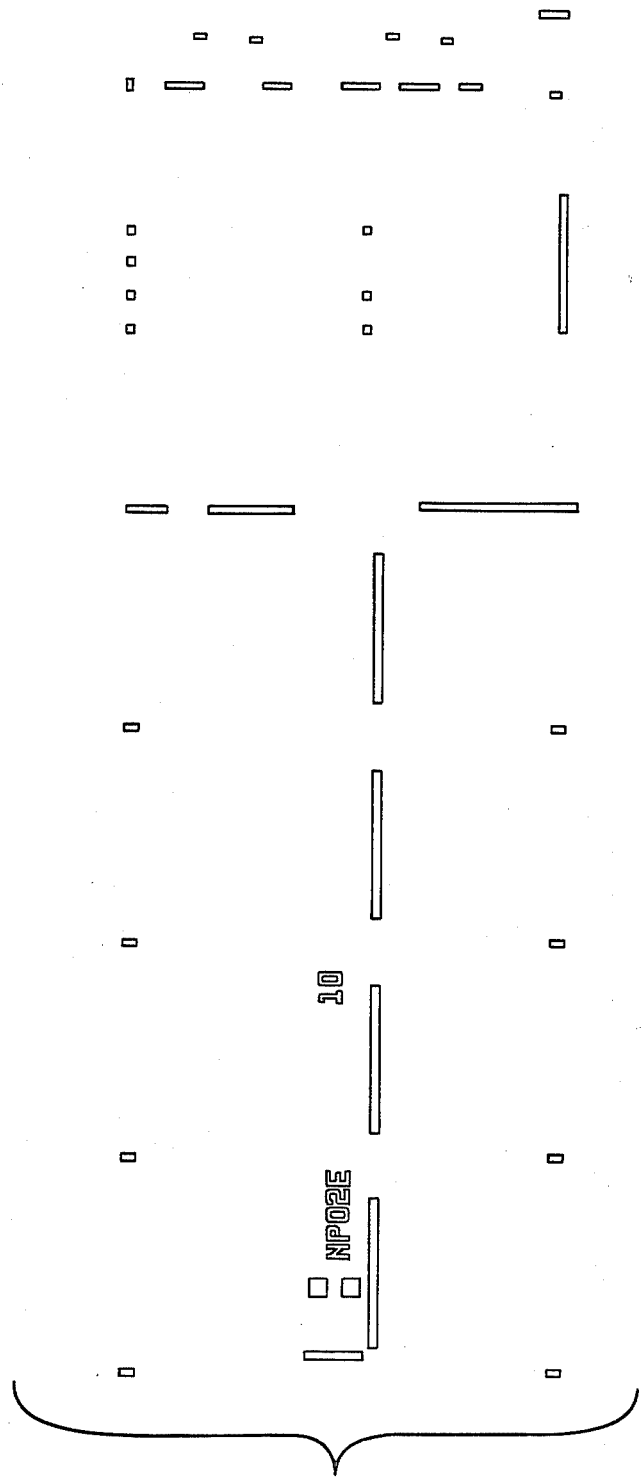
FIG. IIG
(MASK LAYOUT 10)
Ⓜ RICHARD BLAINE BROWN (MASK LAYOUT 5)
Ⓜ RICHARD BLAINE BROWN

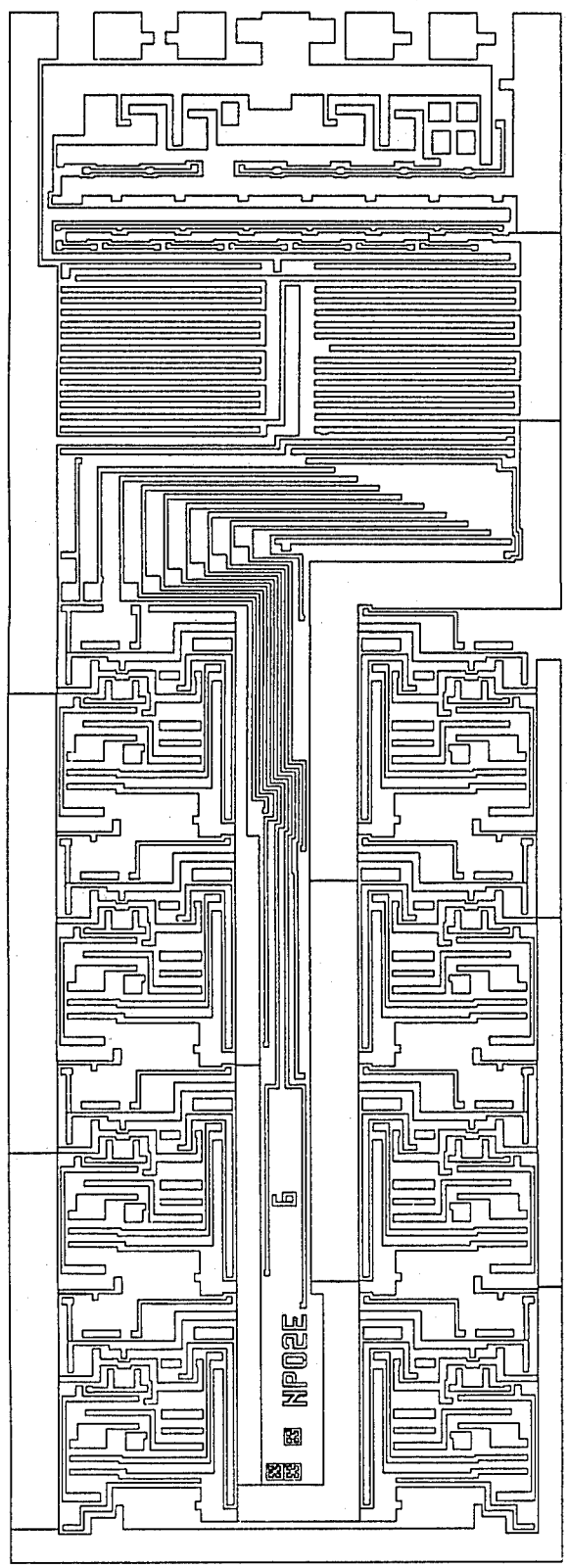
FIG. III
(MASK LAYOUT 6)
Ⓜ RICHARD BLAINE BROWN

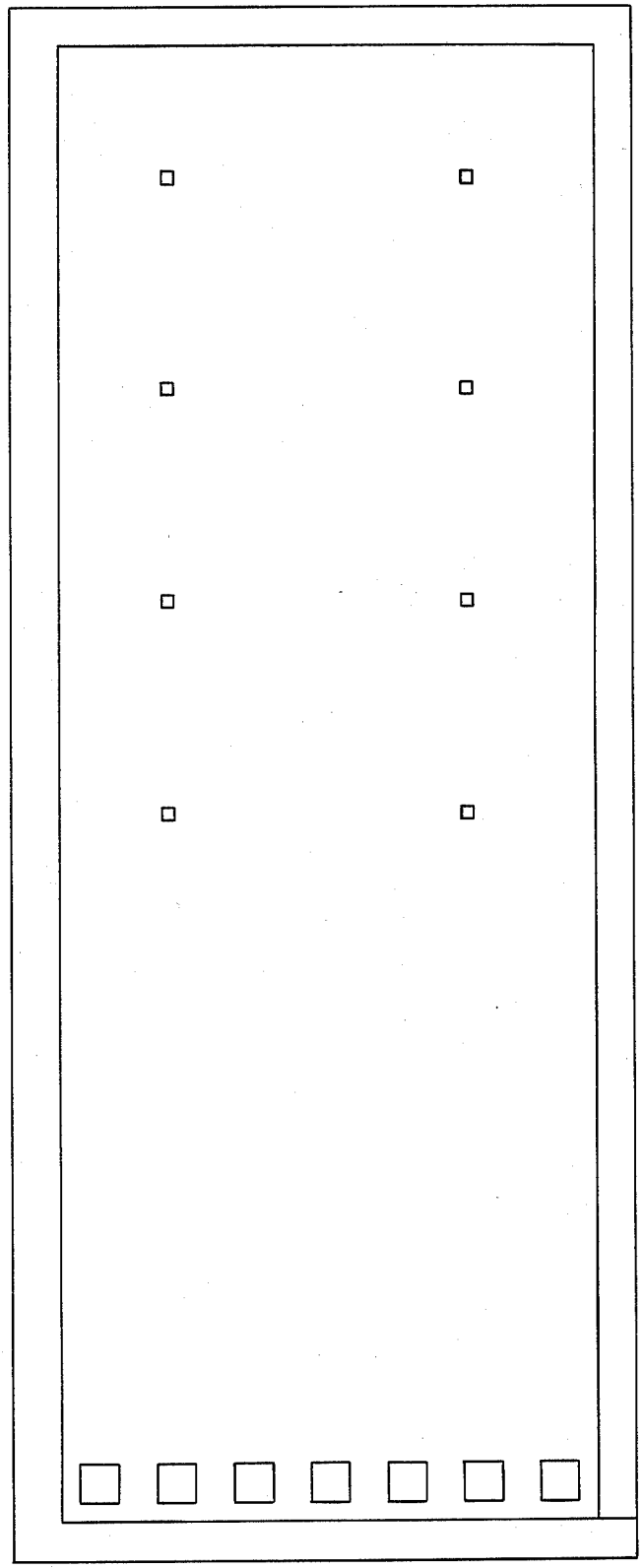
FIG. IIJ
(MASK LAYOUT 7)
Ⓜ RICHARD BLAINE BROWN

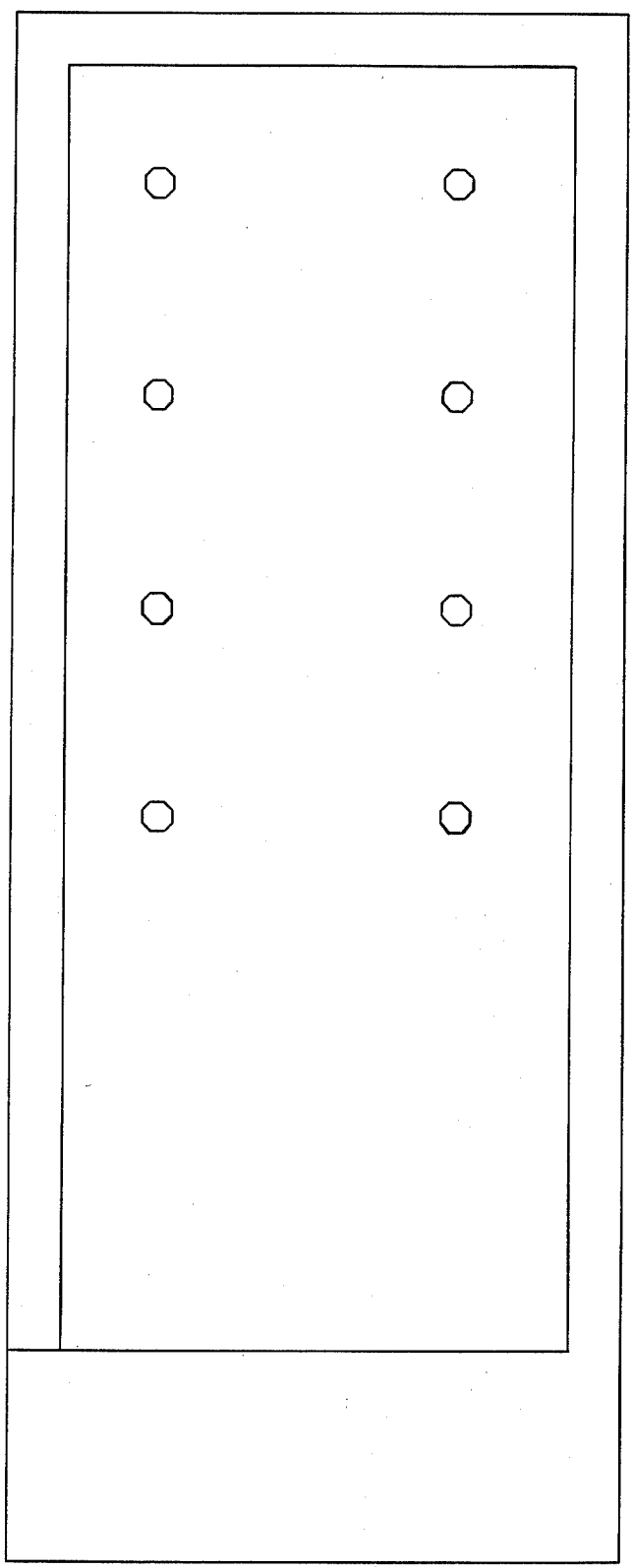
FIG. IIK
(MASK LAYOUT 14)
Ⓜ RICHARD BLAINE BROWN (MASK LAYOUT 17)
Ⓜ RICHARD BLAINE BROWN

INTEGRATED CIRCUIT FOR A CHEMICAL-SELECTIVE SENSOR WITH VOLTAGE OUTPUT

A portion of the disclosure of this patent document contains material to which a claim of mask work protection is made. The mask work owner has no objection to the facsimile reproduction by anyone of the patent document or the patent disclosure, as it appears in the Patent and Trademark Office patent file or records, but reserves all other mask work rights.

BACKGROUND

I. The Field of the Invention

This invention relates to solid-state chemical sensors, and more particularly to a solid-state chemical sensor fabricated on an integrated circuit. An embodiment is included in which the integrated circuit incorporates a plurality of chemical-selective sensors, and related circuitry, for producing an output voltage corresponding to the chemical activity found at one or more of the sensors.

II. The Prior Art

A. Historical Development

One of the most active research areas in the field of analytical measurement is the development of chemical sensors with selectivity for specific ions, gases, biological materials and other substances. Ion selective electrodes (ISEs) have been in use since the discovery, early in this century, of the ion selective properties of the glass/electrolyte interface. ISEs have been popular because of their relatively low cost, wide dynamic range, ease of use and versatility.

During the past decade, a new generation of miniaturized solid-state chemical sensors has evolved which are the progeny of electrochemistry and solid-state electronics. Development of these solid-state chemical transducers was originally motivated by the need for better monitoring of ion activity in biological environments. Medical uses are still seen as among the most promising applications for these solid-state chemical transducers, with researchers hoping to monitor a variety of electrolytes, blood gases, immunochemical agents, and metabolic substrates. Such miniaturized, implantable chemical sensors can aid in the study of biochemical processes and serve as the transducers in biochemical control systems, as well as helping physicians to make proper diagnoses and to maintain homeostasis in critically ill patients.

In addition to the desirable features of the ion selective electrode, the new generation of miniaturized solid-state chemical transducers has the added advantages of inherent impedance transformation, which reduces electrical noise, as well as miniaturization and potentially low-cost mass production made possible through the use of integrated circuit manufacturing processes. Thus, in addition to their use in biochemical applications, miniaturized solid-state chemical transducers are also beginning to be recognized as having many potentially useful applications in addition to biochemistry, such as monitoring pollutants in the atmosphere, public water supplies and industrial effluents; measuring hardness in boiler feed waters; on-line analysis of industrial processes such as electroplating, photographic processing, and the manufacture of foodstuffs and medicines; and in analytical laboratory instruments. In short, while there remain certain restrictions on the chemicals which can be detected using these solid-state chemical sensors, nevertheless many applications in medical and industrial instrumentation could greatly benefit from the use of such miniaturized solid-state chemical transducers.

B. CHEMFET Features

One of the most studied and most successful sensors from this new generation of miniaturized solid-state chemical transducers has been the chemical sensitive field-effect transistor, or CHEMFET. The structure and operation of the CHEMFET is similar in many ways to the structure and operation of a customary insulated gate field-effect transistor, or IGFET. A simplified diagram showing the structure of a CHEMFET is depicted in FIG. 1. This diagram is representative of the CHEMFETS that can be found in the prior art and is essentially the device described in U.S. Pat. No. 4,020,830 issued to C. C. Johnson, S. D. Moss and J. Janata entitled "Selective Chemical Sensitive FET Transducers." This patent presents a detailed review of the theory, structure, and operation of the CHEMFET as found in the prior art.

An appreciation of the operation of the present invention and its advantages over the devices found in the prior art will be gained by a brief review of the operation and structure of the CHEMFET. CHEMFET's are made by substituting a chemical-selective membrane as indicated at 10 in FIG. 1, for what would otherwise be the gate electrode of an IGFET. The membrane 10 is designed to interact with certain species of chemicals to develop an electrical potential at the membrane/gate of the CHEMFET, or to change the threshold voltage of the field-effect transistor. In either case the gate-minus-threshold voltage ($V_G - V_T$) is modified.

In the CHEMFET shown in FIG. 1, the CHEMFET is formed using silicon semiconductor fabrication techniques well-known in the art. The silicon substrate is indicated at 8. The substrate 8 is grown with a p-type dopant and into this p-type semiconductor material is diffused two n-type regions, the source 7 and the drain 6. Conductors 7a and 6a are attached to the source and drain regions 7 and 6, and serve as the source and drain terminals. An insulating layer 12 is deposited such that the source and drain terminals 7a and 6a do not contact the p-type substrate 8. An insulating layer 5 is grown with thermal oxidation over substrate 8 in the region between the source and drain diffusion regions 7 and 6. Another insulating layer 5a is also applied over the source and drain terminal conductors 7a and 6a. The area 9 of the substrate 8 between the source and drain diffusion regions 7 and 6 is called the channel region. The insulating layer 5 applied to the substrate 8 above the channel region 9 is termed the gate insulator.

The chemical-selective membrane 10 is applied to the gate insulator 5 in the area above the channel region 9. The membrane 10 occupies the same area as would the gate electrode in a customary insulating gate field-effect transistor. A final encapsulating layer 4 is applied to the exposed surface of the device except for the top portion 11 of membrane 10. Layer 4 provides electrical isolation and prevents the fluid 2 in container 3, into which the CHEMFET is placed, from making electrical contact with internal circuit parts of the CHEMFET.

With the CHEMFET shown in FIG. 1, the membrane 10 electrically responds when a certain chemical, or group of chemicals, contacts the membrane 10 thus causing a corresponding modulation of the electric field through the gate insulator 5, and consequently a modulation of conductivity in the channel region 9 of the transistor. In this way the electrical response of the CHEMFET represents the chemical activity (i.e., concentration of ionized chemical) found at the surface 11 of membrane 10. A reference electrode 1 is placed into the fluid so as to provide a reference against which the CHEMFET's voltage measurements may be compared.

Three different types of chemical-selective membranes have been proposed for use in solid-state chemical sensors. The first of these senses electrically neutral molecules. The presence of electrically neutral molecules reversibly changes the work function of certain gate materials which absorb them. Materials such as palladium, platinum, and nickel have been tested as gate materials. For example, hydrogen and compounds of hydrogen have been successfully sensed using palladium as the gate material. The work function of palladium (the term work function referring to the potential required to cause emission of an electron from the surface of a material) has been shown to change by 1,240 millivolts when exposed to hydrogen at a pressure of one atmosphere.

A second suggested type of membrane material used for measuring chemical activity with a solid-state chemical sensor is based upon solution/insulator interface theory utilizing polarized interfaces. The potential across the solution/membrane interface is a function of charge which accumulates on the solution side of the interface. With such a membrane, excess charge density on the surface of the interface will be related to chemical activity in a predictable way. However, polarized interface materials presently available in the art have not yet proven to be practical for use in analytical applications.

A third type of chemical-selective membrane material employs a semi-permeable membrane. The membrane is designed to allow certain charged molecules to cross the membrane/solution interface while blocking others. Membranes of this type are referred to as ion-selective membranes. The charged molecules, or ions, migrate across the semi-permeable surface of the membrane until an equilibrium is reached where enough ions have migrated into or out of the membrane to make the electrochemical potential of the ions in the membrane equal to the electrochemical potential of ions in the fluid being analyzed. The potential created by migration of the ions is utilized to modulate the channel region 9 and hence the electric signal produced by the chemical sensor. When the potential found at the chemical sensor is compared to the voltage of a reference electrode placed in the same fluid as the membrane, the activity of the particular ion to which the membrane responds may be readily determined since the membrane voltage is related to the activity of the ion by a simple logarithmic relationship.

Of the three chemical-selective membrane types found in the prior art, the ion-selective membrane has been used most successfully to date. A wide variety of materials for use in ion-selective membranes have been used to sense ions of hydrogen, potassium, calcium, sodium, ammonium, fluoride, and other ions. Furthermore, ion-selective membranes present the possibility that more complex molecules can be detected by using an enzyme or bacterial overlay on the ion-selective membrane where one of the products of the action of the enzyme or bacteria is that to which the ion-selective membrane responds. As used hereinafter, the term chemical-selective membrane is hereby defined to mean any chemical-selective material which is capable of producing an electrical signal that is linearly or non-linearly proportional to a concentration of at least one chemical.

Compared to conventional methods of chemical analysis, solid-state sensors such as the CHEMFET provide a number of advantages, including small size, solid-state construction, inherent impedance transformation, and comparatively low cost. The small size of miniaturized solid-state chemical sensors opens up the possibility of in vivo monitoring of biological fluids. When used for in vivo monitoring, miniaturized sensors may be mounted on a catheter and inserted directly into a patient's blood vessel, or other body structure, to provide constantly updated reports on the patient's blood chemistry or analysis of other body fluid.

Furthermore, a miniaturized chemical sensor has advantages when used for in vitro applications, such as in analytical laboratory measurements. These advantages include: allowing the use of smaller samples; lower device capacitances which allow higher bandwith operation; and a smal sensing surface allowing tracking of local changes in chemical activity rather than averaging chemical activity over a large area. Furthermore, only a small amount of chemical-selective membrane material is needed which can be very important when such materials are expensive. Thus, the advantages of a miniaturized solid-state chemical sensor over other analytical methods are potentially so numerous that in recent years a great deal of research has been devoted toward the development of miniaturized solid-state sensors, miniaturization being an important goal in order to increase the number of potential applications of solid-state chemical sensors.

Solid-state chemical sensors provide other advantages including the fact that solid-state construction provides a mechanically robust sensor which can be used in high pressure, or high vibration environments. Also, since the solid-state chemical sensor is not filled with fluid, as compared to conventional ion-selective electrodes, high temperature operation is possible. Still further, sterilization of solid-state chemical sensors for use in medical applications is easier because no filling fluid is involved.

C. Problems and Shortcomings of the Prior Art

Despite these potential advantages, solid-state chemical sensors presently available in the art suffer from several serious drawbacks which have prevented such sensors from being fully utilized in industrial, scientific and medical applications. These problems include errors introduced into the sensor's output signal due to imperfectly selective membranes or due to signal drift because of aging, temperature or ambient light conditions, and difficulties in fabricating the sensors.

1. Signal Error Due to Imperfectly Selective Membranes

One of the difficulties encountered is that the electric signal derived from a solid-state chemical sensor is typically subject to error signals from several sources. One of these sources stems from the fact that no membrane is perfectly selective to a particular chemical or ion and the electric signal provided by the chemical-selective membrane will include responses due to interfering chemicals. This interference is a serious limitation and it compromises the accuracy of such sensors. This means, for example, that a CHEMFET made to respond to pH might also show a response to sodium. Thus, using a single ion-selective electrode or other chemical sensor in an environment containing two substances to which the chemical-selective membrane responds creates a situation in which there is one equation and two unknowns.

Efforts have been made in the prior art to solve this problem in connection with ion-selective electrodes by using a variation of null point potentiometry which is compensated for interferences, called concentration matching. This technique requires that the test sample be split into two parts, each of which is probed by the same type of sensor. Differences in the ion selective electrodes are taken into account by noting the difference in membrane potentials with identical samples. This provides the so-called null point. One of the ion selective electrodes is then placed in a solvent, to which is added analyte and interferant until the null point is again reached. Arriving at the correct blend of concentrations can only be done by using a simplex optimization, or a polynomial equation solving routine to guide the additions. This procedure is tedious but in the past has been the most successful technique for dealing with interferences in ion selective electrode analysis. However, this technique is ill suited for use with the new miniaturized solid-state chemical sensors, which, as mentioned, hold the promise of continuous monitoring of chemical changes, both in vivo and with flow injection analysis. Concentration matching is neither a real-time process, nor can it be done in vivo.

Another approach to solving the problem of error signals which are caused by interfering ions arises from the possibility of making probes with multiple sensors, so that the interferences can be resolved. For example, if a probe had a second sensor with different sensitivities to one or both of the chemicals involved, two equations would be produced, allowing solution for both unknowns. While this approach potentially holds promise and has been discussed for years, the full development of multisensors has been impeded by: the number of contacts required for parallel connection to the sensors; the time delay to stable operation if sensors and reference voltage are multiplexed; the amount of area on an integrated circuit taken up by a CHEMFET in order to improve transconductance; and limitations on gate size and gate-to-contact spacing for application of certain ion selective membranes. Thus, to date there has not been a satisfactory solution to the problem of compensating for noise signals from interfering ions when using ion selective membranes.

2. Signal Error Due to Drift

Another source of error when using a CHEMFET or solid-state chemical sensor arises because of signal drift with time, temperature and ambient light. The characteristic drift with time has been attributed to mass transport and potential-dependent interfacial ion-crossing kinetics. Thermal sensitivity and photo-induced junction currents cause calibration drifts with ambient changes. Efforts to eliminate light and temperature sensitivity with on-chip compensating circuitry have not been entirely successful because of the inability to precisely match the electrical characteristics (e.g., transconductance) of the CHEMFET to metal oxide semiconductor field effect transistors (MOSFETS) which are typically placed on the integrated circuit to provide compensation. Moreover, since the output signal from a CHEMFET is current, errors can also be introduced by the source and drain resistances, which are also functions of temperature.

3. Fabrication Difficulties

In addition to the above-mentioned problems, other problems which have impeded the use of solid-state chemical sensors such as the CHEMFET have arisen because of fabrication difficulties. One of the principal problems with respect to fabrication arises because of the need for an encapsulation layer which is required to prevent electrical leakage and chemical attack at the sides and back of the sensor when it is exposed to its working environment. These encapsulation procedures are typically manual operations which are extremely difficult to perform with uniformity of results. Another problem is that preparation of the membrane definition layer into which the chemical-selective membrane is deposited and held is also typically a non-planar, manual process. Since solid-state chemical sensors such as the CHEMFET has thus far shown relatively short lifetimes, reducing manufacturing costs is vital to their economic feasibility. More efficient methods of encapsulation and membrane definition are therefore essential.

In summary, the problems discussed above have posed significant obstacles to the wide-scale adoption and use of solid-state chemical sensors, and in particular CHEMFETS, as a practical method of chemical analysis.

BRIEF SUMMARY AND OBJECTS OF THE INVENTION

In light of the present state of the art, a primary object of the present invention is to provide a novel solid-state chemical sensor which is well-suited for implementation in an integrated circuit and which may incorporate multiple solid-state chemical sensors so as to be capable of providing information needed to reduce errors from interfering chemicals.

Another important object of the present invention is to provide a novel approach to integrated circuit design for a solid-state chemical sensor which will reduce signal errors due to changes in temperature, light and aging.

Still another important object of the present invention is to provide a novel integrated circuit design for a solid-state chemical sensor wherein multiple sensors are provided on a single integrated circuit with a minimum number of external connections.

Another important object of the present invention is to provide a novel integrated circuit for chemical analysis using multiple chemical-selective sensors with voltage outputs, and which is sufficiently small to be easily adapted for in vivo use and which can be economically and reliably produced in mass.

Another object is to provide an improved fabrication process for a solid-state chemical sensor wherein the membrane definition steps can be adapted to a planar process rather than requiring manual operations.

The foregoing and other objects and features of the present invention are realized in a novel solid-state chemical sensor which is fabricated upon a silicon substrate as part of an integrated circuit. The solid-state chemical sensor is provided with a chemical-selective membrane. The chemical-selective membrane provides an electric signal in response to contact with a particular chemical or group of chemicals. The electric signal provided by the chemical-selective membrane is designed as an integrated input to a voltage-follower amplifier. The amplifier provides a unity gain buffer and impedance transformation of the electric signal. The output of the chemical sensor is a low impedance electric signal represented as a voltage which corresponds to the chemical activity present at the chemical-selective membrane. In one embodiment, multiple chemical sensors are fabricated on a single piece of silicon as an integrated circuit which includes eight chemical-selective membranes each providing an integrated input to a separate amplifier. Included in the integrated circuit are components to allow for the multiplexing of the outputs of the amplifiers to one or both of two output pads provided on the integrated circuit.

The foregoing and other objects and features of the present invention will become more fully apparent from the following description and appended claims taken in conjunction with the accompanying drawings.

BRIEF DESCRIPTION OF THE DRAWINGS

FIGS. 11A-11L are schematic drawings of the mask layouts used in fabricating one presently preferred embodiment of the solid-state chemical sensor as described in Example 1 below.

DETAILED DESCRIPTION OF THE PRESENTLY PREFERRED EMBODIMENTS

Figure 1:
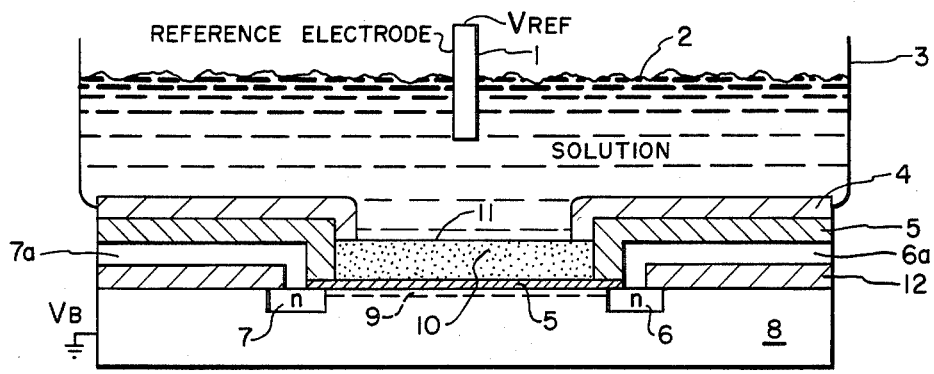
FIG. 1 is a cross-sectional representation of a prior art CHEMFET device.
Figure 2:
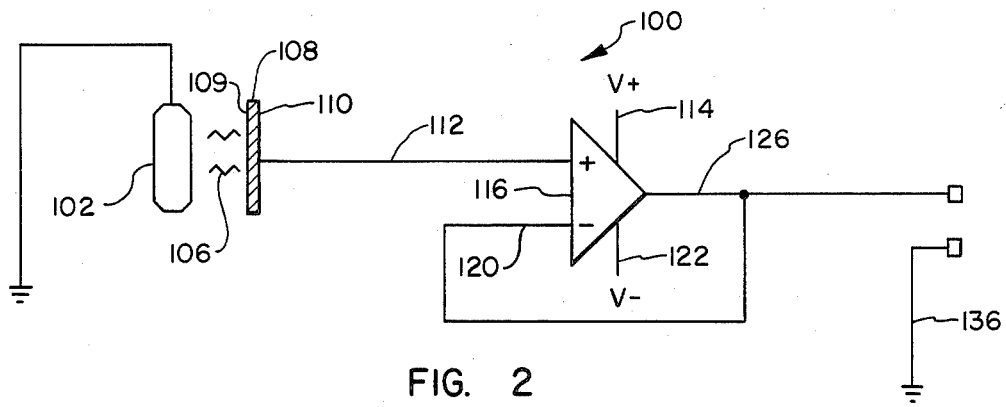
FIG. 2 is a schematic diagram of the novel integrated circuit design for the chemical sensor of the present invention.
Figure 3:
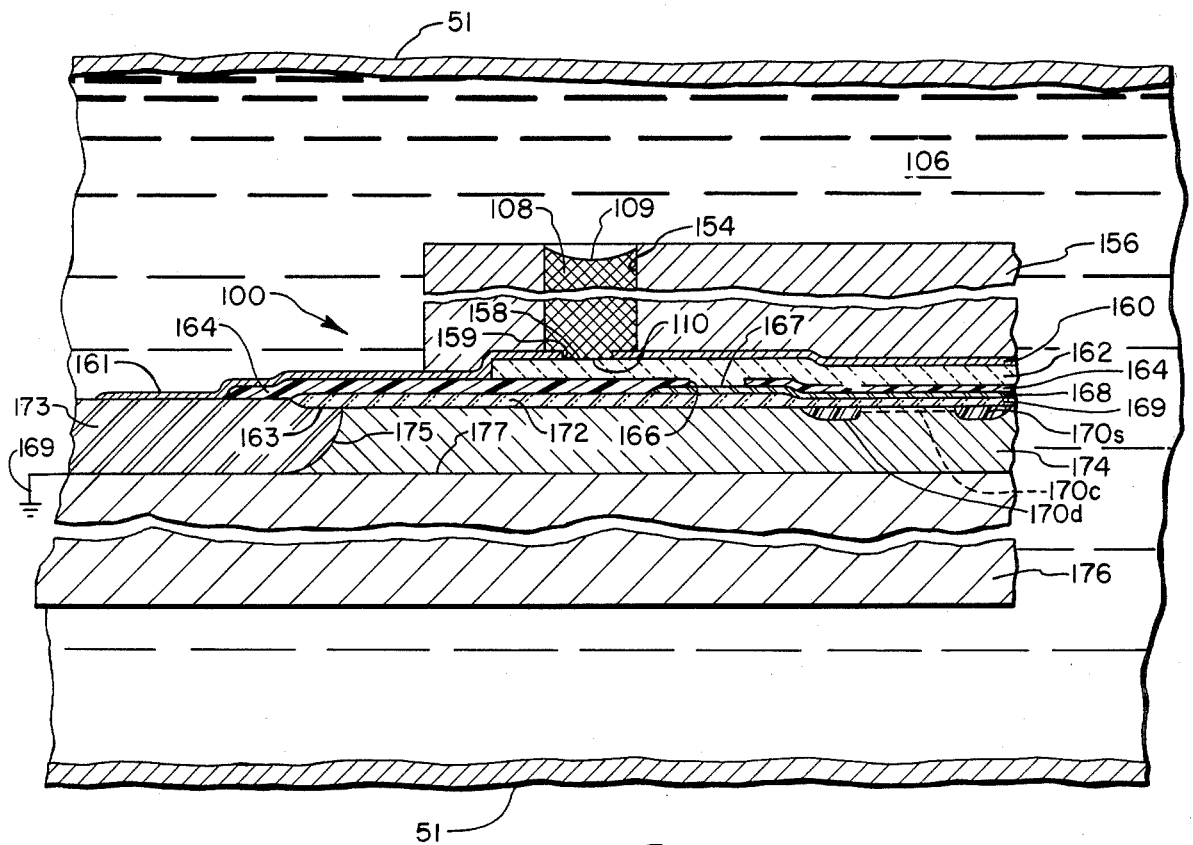
FIG. 3 is a view showing a cross section of a portion of one presently preferred embodiment of an integrated circuit which incorporates the circuit design of the chemical sensor of the present invention.
Figure 4:
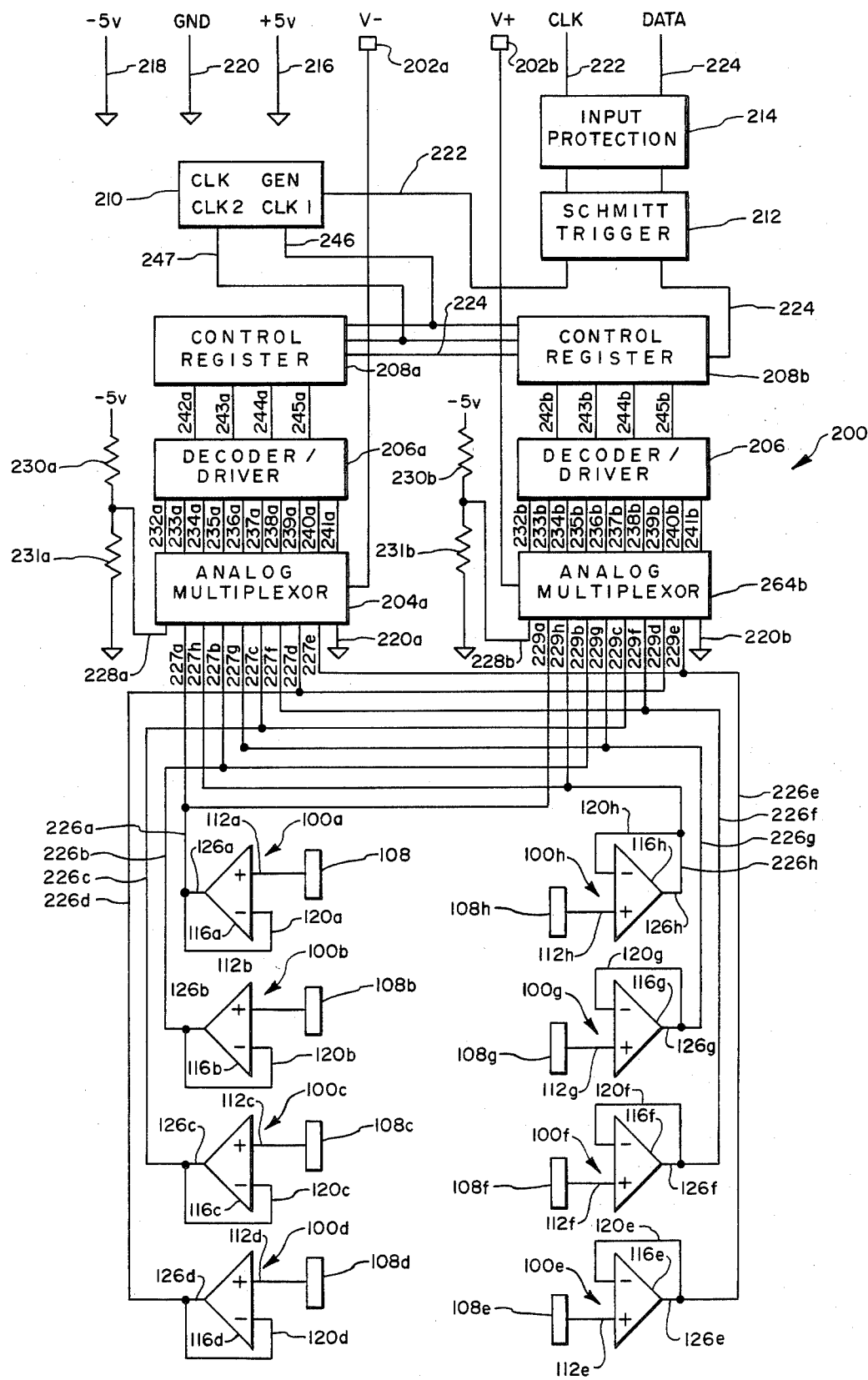
FIG. 4 is a block diagram of one presently preferred embodiment of the invention in which an integrated circuit is provided with eight individual chemical sensors.

The following detailed description will be divided into three parts. The first part will discuss the basic integrated circuit design for the solid-state chemical sensor as shown schematically in FIGS. 2 and 3. Next, the structure and operation of the embodiment shown in FIG. 4 is described. In that embodiment eight chemical sensors, each incorporating the novel integrated circuit design shown in FIGS. 2 and 3, are incorporated onto a single silicon chip. Last, the method of fabricating the integrated circuit will be discussed, including the masks and process steps used to fabricate the integrated circuit incorporating the embodiment of FIG. 4 of the present invention.

I. The Basic Integrated Circuit Design for the Solid-State Chemical Sensor

The integrated circuit design for the presently preferred embodiment of the chemical sensor of the present invention is generally indicated at 100 in FIG. 2. The chemical sensor 100 comprises a reference electrode 102, a chemical-selective membrane 108 and an amplifier 116.

The chemical-selective membrane 108 on sensor 100 is in contact with a fluid 106 and is electrically connected to an amplifier 116 as indicated at 112 so as to provide an integrated input to the non-inverting terminal of amplifier 116. As used herein and as hereinafter more fully explained, the term integrated input is defined as meaning the voltage produced by the membrane 108 where the membrane 108 is not used as the gate of any field-effect transistor, and where said voltage is electrically input to the amplifier 116 by an electrical connection formed on a semiconductor substrate between both the membrane 108 and amplifier 116. Also, as used herein, the term fluid includes both liquids and gases. The output 126 of amplifier 116 reflects the potential found at membrane 110 which corresponds to the activity of the particular chemical, or chemicals, to be sensed in the fluid 106. Thus, at the output 126 the voltage, when measured against the potential found on the reference electrode 102, is proportional to the chemical activity (i.e., concentration of the particular chemical or chemicals) sensed at membrane 108.

Reference electrode 102 provides a reference potential against which the output 126 of the chemical sensor may be measured. The reference electrode 102 may be of any resistive material which is electrochemically stable in the fluid 106. Furthermore, the reference electrode 102 may be placed at ground potential thereby allowing the output voltage to also be measured with reference to ground. This is particularly advantageous when the chemical sensor is to be used for in vivo application since placing an electric potential other than ground in a patient's body is undesirable and can be hazardous. In other applications, the reference electrode 102 may be placed at potentials either above or below ground potential.

The membrane 108 must be attached such that only one side 109 of the membrane is exposed to the fluid. While many different configurations of membranes could be used, a generally planar configuration has been found to be advantageous since it facilitates the planar process used in fabricating the integrated circuit, as discussed further in part III. Any membrane with the desired chemically selective characteristic can be utilized in the present invention. It should be appreciated that the present invention can be used with any of the chemical-selective membranes presently available in the art, as discussed earlier.

As hereinafter explained in greater detail, the chemical sensor 100 is hermetically sealed around the edges of the membrane 108 such that the fluid 106 is not capable of contacting the reverse side 110 of the membrane 108. The electrical connection to the reverse side 110 of membrane 108 is provided by a low resistance contact. Thus, any potential created at the fluid/membrane interface 109 is transferred through the membrane 108 and is input on the non-inverting terminal of amplifier 116.

FIG. 3 schematically illustrates a cross-sectional view of the integrated circuit which incorporates the basic circuit design of the chemical sensor 100 shown in FIG. 2. In FIG. 3, the chemical sensor 100 is shown in a fluid 106 such as blood, the walls of the blood vessel being indicated at 51. The drawing is greatly enlarged and is not to scale in order to show sufficient detail. The structure shown in FIG. 3 may be fabricated by a process which will be discussed later in part III of this specification.

In the presently preferred embodiment, a conventional wafer (not shown) is prepared having a substrate 176 of n-type silicon. An epitaxial layer 174 of p-type silicon is grown on the substrate 176. A junction isolation layer 173 is diffused around the periphery of the integrated circuit. As described more fully in parts II and III, the junction isolation layer 173 and substrate 176 are of n-type silicon and may be connected to ground as schematically indicated at 169. Layer 173 and substrate 176 together provide electrical and chemical isolation of the active circuitry without having to encapsulate the sides and back of the solid-state sensor using time-consuming and tedious manual steps. Thus, as shown at 163 the junction isolation layer 173 should be slightly overlapped by the layers 169 and 164.

A field oxide layer 172 is next formed everywhere except those areas defined as active areas 170d (the drain), 170s (the source) and 170c (the channel). Upon the active area layer 170 there is grown a thermal-oxide layer 169 which serves as a gate insulator for a field-effect transistor whose channel region is formed in the active area 170c. Upon the gate oxide layer 169 and partially upon the field-oxide layer 172 there is deposited a conducting layer of polysilicon 168.

A layer 164 of pyro oxide is next formed over the polysilicon layer 168, the gate oxide layer 169 and field oxide layer 172. A contact hole 166 is opened in the pyro oxide layer 164 such that a portion 167 of the polysilicon layer 168 is left uncovered. Upon the pyro oxide layer 168, the uncovered portion 167 of the polysilicon layer 168, and upon diffusion area 170d and 170s, there is then deposited a metal layer 162. In the presently preferred embodiment the metal is silver or platinum over aluminum. A passivation layer of silicon nitride 160 is then deposited upon the entire surface and an opening 159 is formed to expose a portion of the metal layer 162 which will serve as a membrane contact or input pad, indicated at 158. The passivation layer 160 chemically and electrically isolates the top side of the circuit and should overlap the junction isolation layer 173 as indicated at 161. The membrane definition layer 156 is then formed upon all the remaining layers.

A membrane well 154 is opened in the layer 156. The chemical-selective membrane 108 is placed into the well 154. The location of the membrane well 154 corresponds to the exposed metal contact 158 exposed by the opening 159 in the silicon nitride passivation layer 160. The membrane definition layer 156 provides an hermetic seal with the sides of the chemical-selective membrane 108 such that the fluid 106 cannot leak to the reverse side 110 (see also FIG. 2) of the chemical-selective membrane 108 and disrupt the electrical contact between the chemical-selective membrane 108 and the metal layer contact 158.

With further reference to FIG. 3, a potential that is developed at the fluid/membrane interface 109 will be conducted to the reverse side 110 of the membrane 108 at which point the membrane is contacted at 158 by the metal layer 162. The metal layer 162 then is able to transfer any potential from membrane 108 to the polysilicon layer 168 through contact 167. The polysilicon layer 168 serves as the gate electrode of an input transistor of the amplifier 116 shown in FIG. 2 as hereinafter more fully explained in connection with FIG. 5A. The gate insulator is formed by the oxide layer 169, and the active area 170c forms the channel region of the input field-effect transistor of amplifier 116.

The amplifier 116 is provided with connections 114 and 122 to supply operating voltage and current to the amplifier, as shown in FIG. 2. The integrated input 112 leading from the chemical-selective membrane 108 to the amplifier 116 is provided by the metal layer 162 (see FIG. 3) and contact portions 158 and 167 which connect the metal layer 162 to the membrane 108 and gate insulator layer 168 of the transistor serving as the input transistor for the non-inverting input of the amplifier 116, as hereinafter more fully described.

The amplifier 116, as shown in FIG. 2, is configured to operate in a voltage-follower mode. In such a configuration, the output 126 of the amplifier 116 is tied as indicated at 120 to the inverting input of amplifier 116. The use of an amplifier configured in this fashion provides for beneficial impedance transformation and stability in the circuit as will be explained in greater detail below.

Figure 5A:
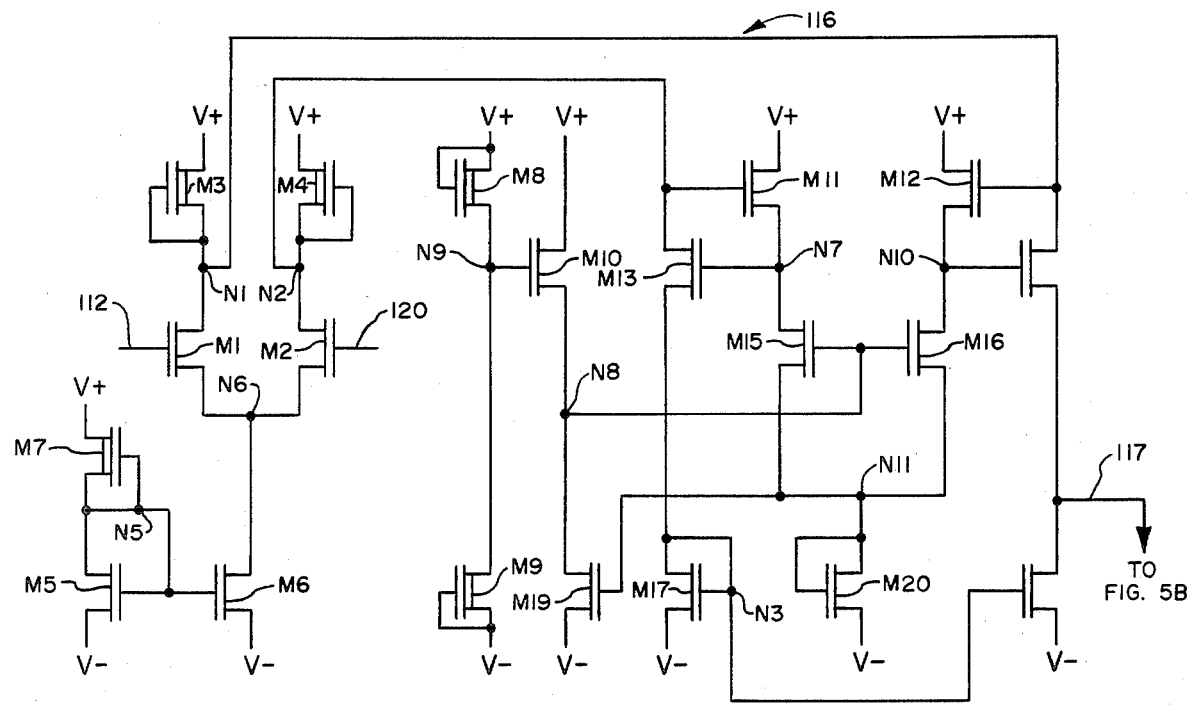
FIG. 5A is a schematic diagram of the differential input and level shifter stages of the operational amplifier used in one presently preferred embodiment of the present invention.
Figure 5B:
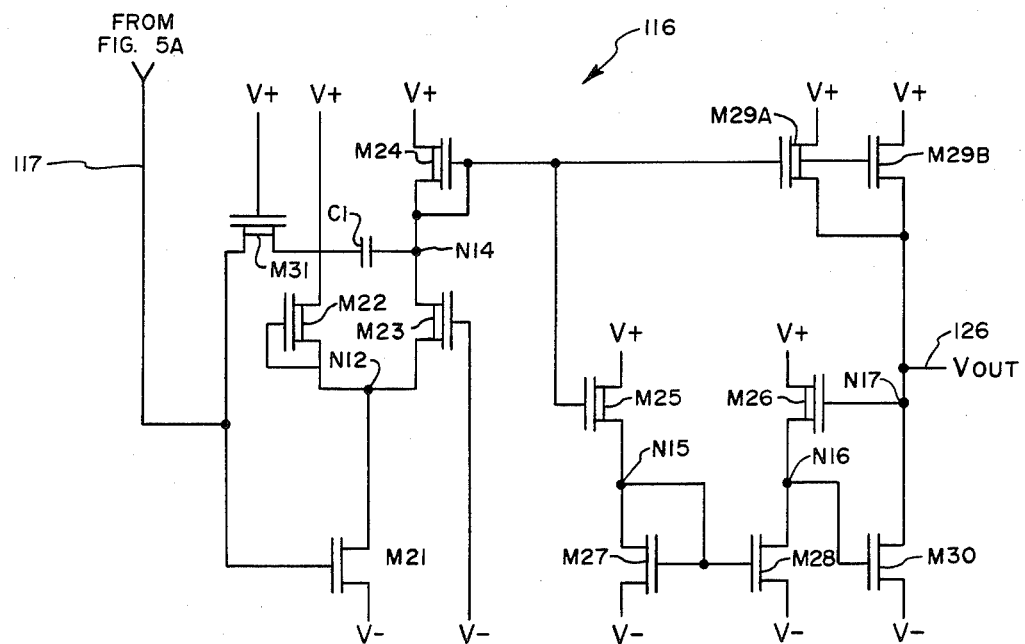
FIG. 5B is a schematic diagram of the integrator and output stages of the operational amplifier used in one presently preferred embodiment of the present invention.

The design of the amplifier 116 which has been adapted for use in the presently preferred embodiment is one that is commonly available in the art of integrated circuit design. The design originated with D. Senderowicz, D. A. Hodges and P. R. Gray. Further details concerning the amplifier are available in the publication *Analog MOS Integrated Circuits* (I.E.E.E. Press 1980, pp. 56–62), incorporated herein by reference. FIGS. 5A and 5B show the detailed schematic circuit representation of the amplifier 116 adapted for use in the chemical sensor of the present invention. Various other amplifier designs could be used in the present invention.

The drawings showing the detailed schematic circuit diagrams are marked with alphanumeric designations that are commonly used in the art of integrated circuit fabrication. The designation for transistors is an "M", for resistors "R", for capacitors "C", and for nodes in the circuit "N". The alphanumeric designations are included so that easy reference to other materials included in the appendices hereto may be made.

Referring first to FIG. 5A, transistors M1 through M7 comprise the differential input stage of the amplifier 116 with M5 to M7 forming what is known in the art as a Wilson current source. The Wilson current source provides a constant drain current as M6. M1 and M2 are the input transistors of the amplifier 116. M1 functions as the non-inverting input and is connected to the membrane 108, M2 functions as the inverting input. The gate of transistor M2 is connected to the output of amplifier 116 so as to provide the voltage-follower configuration for the amplifier. Both M1 and M2 are field-effect transistors which must have essentially identical dimensions and gate materials. By fabricating M1 and M2 side-by-side on the same semiconductor chip, both transistors can be matched so as to exhibit essentially identical characteristics.

Importantly, it should be noted that the chemical-selective membrane 108 in the circuit design of the present invention does not serve as the gate of a field-effect transistor. In this sense, the sensor of the present invention is not, strictly speaking, a CHEMFET. Rather, the membrane 108 is electrically connected by means of metal layer 162 (see FIG. 2) to the gate of transistor M1. Thus, in this sense the voltage of membrane 108 is provided as an integrated input to the amplifier 116. This eliminates the difficulty heretofore experienced in the prior art with CHEMFET devices in having to match the transconductance of the CHEMFET to a MOSFET. In the sensor of this invention, since the membrane 108 does not serve as an insulated gate for either M1 or M2, M1 and M2 are easily matched. Thus, compensation for drift due to aging, light or temperature variations is significantly improved in the sensor of the present invention.

Transistors M8 to M20 comprise the level shifter stage of the amplifier. This stage shifts the level of the differential signal so that it is referenced against the supply voltage. The level shifted signal is applied as indicated at 117 to the integrator stage, comprising transistors M21, M23 and M31 as well as capacitor C1 (see FIG. 5B). The function of the integrator stage is principally to provide gain. This function is mainly carried out by transistor M21, which is a relatively large transistor. Thus, M21 exhibits a high transconductance. The output of the integrator appears at node N14.

Transistors M24–M30 comprise the output stage and function to reduce the high impedance output from the integrator stage to an impedance on the order of 100 ohms or less.

When connected as shown in FIG. 2, the output 126 of the amplifier 116 will follow the voltage of the electric signal produced by the chemical-selective membrane 108. This configuration of the amplifier 116 serves a dual function. The most important function is that the output of the sensor 100 is a voltage. This occurs because the amplifier 116 functions as a unity gain buffer. In contrast to the prior art CHEMFETs which provide their output as current, the voltage output of sensor 100 is less sensitive to errors in signal level due to changes in resistance along the output signal path.

The second function served by the amplifier 116 is that of impedance transformation since a very low output impedance is desirable. The chemical-selective membrane 108 has a characteristically high impedance and the amplifier 116 of the presently preferred embodiment matches that high impedance with a characteristically higher impedance found at the gate of the input transistor M1. The amplifier 116 then produces a proportional electric signal at its output 126 which exhibits a characteristic impedance of less than one ohm. This helps make the voltage output less sensitive to external noise, and eliminates the need to shield the conductors carrying the output signal from the chemical sensor. Since shielding is not required, connections to the chemical sensor of the present invention are more easily implemented.

Because of the insulated gate construction of the input transistors M1 and M2 their input impedance is very high, characteristically greater than 10 megohms. A high input impedance is essential for proper operation of the device so as to avoid loading of the electric signal conveyed from the chemical-selective membrane 108.

By providing the chemical-selective membrane 108 as an integrated input to the amplifier 116 rather than forming a discrete CHEMFET, the goal of reliably producing mass quantities of the miniaturized solid-state chemical sensor can be more easily realized, as explained further in part III. Furthermore, by elimination of the discrete CHEMFET used in the prior art chemical sensors, the problem of matching the CHEMFET's characteristics with a MOSFET in order to compensate for drift due to light, temperature or aging has been substantially eliminated. Since all the transistors used in the chemical sensor of the present invention are of the same general type (e.g., silicon gate MOSFETS) and are incorporated on a single semiconductor chip as an integrated circuit, it is much easier to match the characteristics of one transistor with that of another, as needed. Therefore, the problem of matching device characteristics has been largely eliminated in the present invention.

While the chemical sensor of the present invention provides a reliable device which greatly reduces signal error due to drift and which may be incorporated in a very small package making it suitable for use in a variety of biological, industrial and scientific applications, the fact that chemical-selective membranes as presently found in the art are imperfectly selective must still be dealt with. The term "imperfectly selective," as explained above, means that the chemical-selective membrane produces an electrical signal not only in response to the particular chemical whose concentration is desired to be known but also to other interfering chemicals which may be present in the fluid. Furthermore, even if such chemical-selective membranes were perfectly selective, it is of limited use to have a chemical-sensing system which can sense only one chemical. Such a use does not fully utilize the full potential of the solid-state chemical sensing technology. In order to overcome both of these limitations, a multiple chemical sensor embodiment of the present invention was conceived and is described next.

II. Multiple Chemical Sensors On An Integrated Circuit

The embodiment shown in FIG. 4 allows the advantages of incorporating multiple chemical sensors in a single integrated circuit to be gained without losing any of the advantages explained above for the individual solid-state chemical sensor. The integrated circuit 200 shown in FIG. 4 is comprised of eight solid-state chemical sensors 100a–100h. Any number of sensors 100 could be used depending upon the number of chemicals to be sensed and the overall size of circuit 200 that is desired. Each of the individual chemical sensors 100a–100h are identical in their structure to the chemical sensor 100 described in FIGS. 2 and 3, with the exception that different chemical sensors may be fitted with different chemical-selective membranes which may necessitate the membrane wells being of different shapes and sizes.

The integrated circuit 200 is also provided with a means, under the control of an external device such as a central processing unit (CPU), for selectively routing the electric signal from each chemical sensor output 126a–126h to one or both output terminals designated at 202a and 202b. The means for selectively routing each sensor output 126a–126h is comprised of several stages: a multiplexing stage having two analog multiplexors 204a and 204b; a digital decoding stage having two decoder/drivers 206a and 206b; and digital control stage comprising the control registers 208a and 208b, a clock generator 210, a Schmitt trigger 212 and an input protection circuit 214. Also provided are seven input- /output connections which provide a positive voltage supply 216, a negative voltage supply 218, a ground connection 220, outputs 202a–202b, a clock input 222, and a data input 224.

The integrated circuit 200 is fabricated on a single semiconductor chip. The detailed information concerning the dimensions and layout of the transistors and other components found on the integrated circuit, as well as the process steps necessary to fabricate the presently preferred embodiment can be found in tables 1 through 12 and appendices 1 and 2 as well as the accompanying text in part III.

The multiplexing stage, digital decoding stage, and digital control stage together allow the time-division multiplexing of the outputs 126a–126h of the various chemical sensors 100a–100h to one or both of the output terminals 202a and 202b on the integrated circuit 200. Thus, by use of time-division multiplexing eight chemical sensors 100a–100h are included on a single integrated circuit 200 while requiring only seven external connections to the integrated circuit 200. The small number of external connections aids in keeping the overall size of circuit 200 sufficiently small.

Time-division multiplexing of the outputs 126a–126h of the chemical sensors 100a–100h is highly advantageous since without the use of multiplexing techniques six additional output terminals would be needed, bringing the number of external connections to thirteen, almost twice that of the present invention as embodied in circuit 200. The added external connections would complicate and limit use of the sensors for in vivo monitoring, since connections to bonding pads, the portions of the integrated circuit to which external connections are made, would begin to take up a significant amount of area necessitating a larger chip.

It should be appreciated that the scope of the invention encompasses the use of a greater or lesser number of chemical sensors on the integrated circuit. For example, where more than eight sensors 100 are desired, the multiplexing, decoding and digital control stages could be modified accordingly to allow multiplexing of a greater number of chemical sensor output signals.

There are several advantages in providing each chemical-selective membrane 108a–108h as a separate integrated input to a corresponding amplifier 116a–116h, rather than having two or more chemical-selective membranes share one amplifier, although the latter arrangement is also possible and is within the scope of the present invention. First, multiplexing at high speed is possible since the sensors 100a–100h are always active and equilibrium of the various sensors 100a–100h is not upset. Therefore, no time is lost when switching from one sensor to another. In contrast, where a single amplifier is switched between different membranes, some time is required for each sensor to settle into equilibrium.

Second, the input transistors of each chemical sensor are perfectly matched for better compensation of errors due to process variations, temperature changes, and aging. The matching of input transistors allows each of the chemical sensors to be precisely calibrated because each chemical-selective membrane 108a–108h is provided with its own amplifier circuit 116a–116h.

Third, any membrane of suitable type and size can be applied to any one of the sensors. This is possible because by inclusion of an amplifier 116a–116h for each membrane 108a–108h, the current source included in the amplifier is able to set the drain current for the input transistors and guarantee proper biasing of the input transistors independent of the membrane, thus allowing design of the membrane to be independent from design of the electronics and instrumentation. Even with the inclusion of eight independent chemical sensors 100a–100h the circuitry necessary to perform required multiplexing, and the seven external connections provided on the chip, the total area required for fabrication of the chip is only about 54 mils by 140 mils.

Reference will now be made to FIG. 4 for an overview of the operation of the presently preferred embodiment of circuit 200. Each of the eight chemical sensors, generally designated at 100a–100h, has one output 126a–126h. Each of the outputs 126a–126h of the chemical sensors 100a–100h is electrically connected to an analog input 227a–227h and 229a–229h of the analog multiplexors 204a–204b by way of conducting traces represented by lines 226a–226h. The purpose of the analog multiplexors 204a–204b, both of which make up the multiplexing stage, is to provide a switching function such that one of the eight electric signals from the chemical sensors 100a–100h is routed to the output terminals 202a and/or 202b.

Each of the analog multiplexors 204 is provided with ten analog inputs, eight inputs 227a–227h and 229a–229h being for connection to the conducting traces 226a–226h of the chemical sensors 100a–100h, one input 220a and 220b being for connection to ground 220, as well as one analog input 228a and 228b being electrically connected to a resistive voltage divider, formed by resistive traces represented at 230a–231a and 230b–231b.

Each of the analog multiplexors 204 is driven by the digital decoding stage which consists of two digital decoder/drivers 206a–206b. Each of the decoder/drivers 206a and 206b receive a four-bit binary digit word as indicated at 242a–245a and 242b–245b from one of the control registers 208a or 208b and in turn decodes the four-bit binary word and turns on the appropriate decoder/driver digital outputs 232a–241a or 232b–241b to select one of the multiplexor inputs 227a–227h or 229a–229h. When selected, a particular sensor output 126a–126h is then routed by multiplexors 204a and/or 204b to the output terminals 202a and/or 202b.

The control registers 208a and 208b are serially connected as indicated at data input line 224 such that they receive a serial digital data stream from an external source such as a CPU (not shown). Each of the control registers 208 receives and stores four bits of data, the arrangement of the data bits being such that when the four bits are decoded by the respective decoder/driver 206a or 206b, the appropriate analog input 227a–227h or 229a–229h will be selected.

The Schmitt trigger 212 provides a wave-shaping function so that that a "clean" square wave (e.g., sharp leading and trailing edges) reaches the control registers 208 and the clock generator 210. The input protection 216 is provided to ensure that the high impedance gate insulators found at the input transistors of the Schmitt trigger 226 are not damaged if a high voltage inadvertently appears on either the clock 222 or data 224 inputs to the circuit 200. The only dynamic inputs to the circuit 200 are the clock and data inputs 222 and 224, which are under control of the CPU (not shown) and which in turn control the routing and multiplexing functions.

The detailed schematic diagram of each of the individual stages described above will now be explained.

Figure 6:
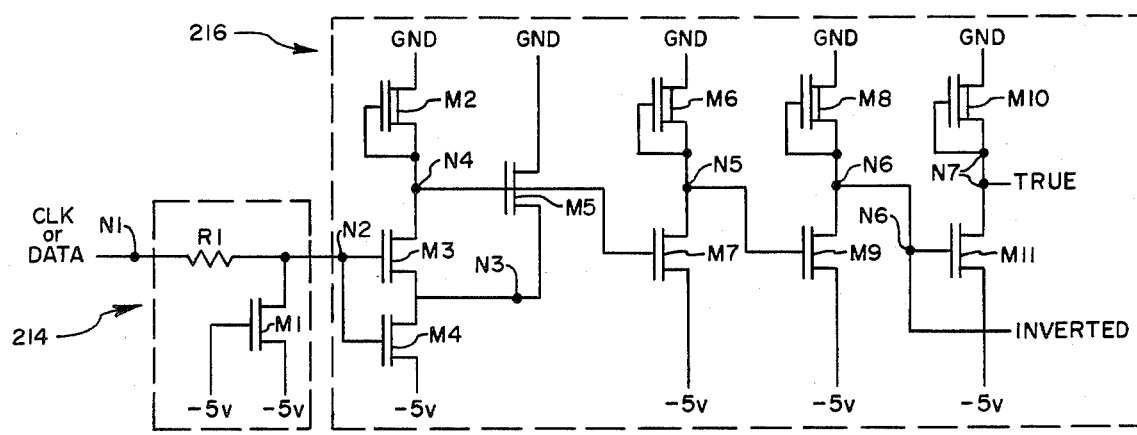
FIG. 6 is a schematic diagram of one of two identical circuits implementing the input protection and Schmitt trigger blocks shown in FIG. 4.

Reference is first made to FIG. 6, which is a schematic diagram of the input protection and Schmitt trigger circuits 214 and 212. FIG. 6 shows only one of two circuits, each of which is identical, which together provide the input protection and wave-shaping for the data input 224 and the clock input 222. The clock and data inputs 222 and 224 pass from the input protection and Schmitt trigger circuits 214 and 212 to the clock generator 210 and control registers 208a-208b as indicated at lines 222 and 224, respectively.

In the circuit of FIG. 6, the input protection function is provided by resistor R1 and transistor M1. The data input 224 or clock input 222 are connected to node N1 in FIG. 6. Resistor R1 has a value of approximately 4000 ohms, and is formed by a diffusion process so as to create a diode junction between the diffused area and the semiconductor substrate (not shown). If the voltage applied to R1 exceeds (in the negative direction) the supply voltage, the diode junction formed by R1 and the semiconductor substrate becomes forward biased thus clamping the voltage to approximately the source voltage minus 0.7 volts in the case of a silicon semiconductor substrate. If the voltage at R1 should reach a positive 15–20 volts, transistor M1 will turn on and clamp the voltage, with R1 acting to limit the current carried by transistor M1.

The Schmitt trigger 226 of FIG. 4 comprises transistors M2 to M5 as shown in FIG. 6. As with the input protection function, both the data 224 and clock 222 inputs are provided with identical circuits that perform a Schmitt trigger function. Furthermore, transistors M6 to M11, as shown in FIG. 6, form a buffer and inverter circuit to provide the voltage gain needed to drive the subsequent stages as well as to provide both the true and inverted outputs as indicated at nodes N7 and N6, respectively, which are used to drive subsequent circuitry. The Schmitt trigger circuit as shown provides a hysteresis of approximately 2 volts with switching points of approximately $-2$ and $-4$ volts.

Figure 7A:
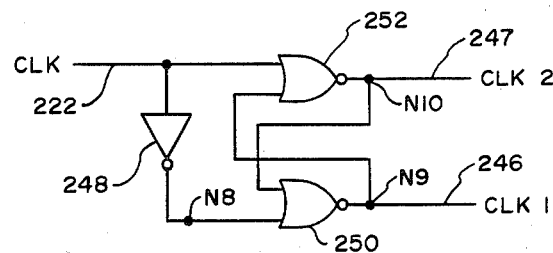
FIG. 7A is a logic diagram representing the implementation of the clock generator block of FIG. 4.
Figure 7B:
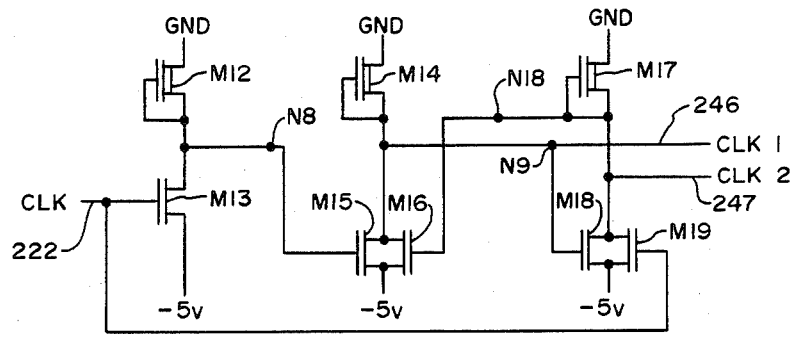
FIG. 7B is a schematic drawing of the circuit implementation of the logic diagram shown in FIG. 7.

FIG. 7A is a logic diagram of the clock generator circuit 210 shown in FIG. 4. FIG. 7B is the schematic diagram of the clock generator 210. The function of the clock generator 210 is to provide, upon detecting a pulse on the clock input 222, a first and second clock signal. The first clock signal (CLK 1) is always in a low state when the second clock signal (CLK 2) is in a high state.

The operation of the clock generator may be best explained by reference to FIG. 7A. When the clock input signal at 222 is in a low state, the output of the inverter 248 will be high and the clock one signal at 246, which is the output of a first NOR gate 250, will be low. At the same time, the clock two signal at 247, which is output from a second NOR gate 252, will be at a low state. When the clock input 222 begins to rise, the clock two signal will immediately drop, yet the clock one signal cannot rise until the output of the inverter 248 enters a low state, which will be a short time after the clock input signal 222 begins to rise. Thus, the logic arrangement shown in FIG. 7A assures that the clock one and clock two signals will not be found in a high state at the same time. These two clock signals prevent a "race" condition from developing in the control registers 208.

FIG. 7B represents the schematic diagram of the logic shown in FIG. 7A. Transistors M12 and M13 comprise the inverter 248, transistors M14 to M16 comprise the first NOR gate 250 and transistors M17 to M19 comprise the second NOR gate 252.

The control registers 208 of FIG. 4 each comprise four identical shift register cells. Each of the shift-register cells are connected to one of the four control register digital outputs 242-245 which are connected to the decoder/drivers 206. Each of the registers 208 is a fully static shift register whose circuit schematic for one cell is shown in FIG. 8.

The use of a fully static shift register, as opposed to the use of a dynamic shift register, while requiring a greater number of transistors, allows the advantage of not requiring dynamic clocks, which might disturb the chemical sensor output. Each cell of the shift registers 208 is serially connected in the following fashion. The SET and RESET nodes N1 and N2 of the first cell (see FIG. 8) are connected to the TRUE and INVERTED outputs at nodes N7 and N6 (see FIG. 6) of the Schmitt trigger circuit. The SET and RESET nodes of the remaining cells are respectively connected to the previous cell's Q and $\overline{Q}$ nodes N9 and N10. By this arrangement, data which is serially entered on the data input 224 is entered into the first cell and then serially shifted down one cell in response to the clock one (CLK 1) and clock two (CLK 2) signals output by the clock generator 210.

When the cell's clock one (CLK 1) input 246 is in a high state, pass transistors M1 and M2 turn on and data is received by the cell through the SET and RESET nodes N1 and N2. Transistors M3 to M8 form a flip-flop circuit as is well-known in the art. While the cell's clock one (CLK 1) input 246 is high, the flip-flop changes state to conform to the SET and RESET signals. After data has been received by the flip-flop circuit, clock one (CLK 1) input 246 will go low and the clock two (CLK 2) input 247 will go high shortly thereafter. When the cell's clock two input 247 goes high, pass transistors M9 and M10 turn on, thus allowing the signal stored in the flip-flop to be applied to the output buffer comprising transistors M11 to M14.

Figure 8:
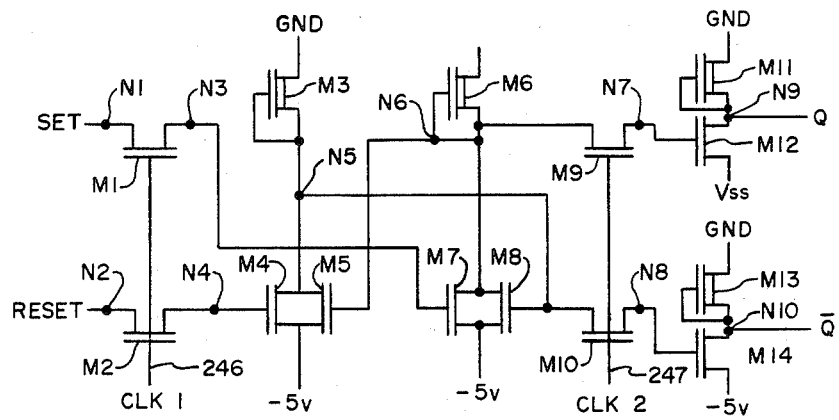
FIG. 8 is a schematic diagram of the circuit of one cell of the control register blocks shown in FIG. 4.

Each of the control registers 208 shown in FIG. 4 includes four shift register cells, each cell arranged as shown in FIG. 8. The Q and $\overline{Q}$ outputs of each of the four cells are respectively designated A, $\overline{A}$, B, $\overline{B}$, C, $\overline{C}$ and D, $\overline{D}$. Thus, each shift register cell of each control register 208 has two output states, making eight output states available at each control register 208. Both the true and inverted outputs of the shift register cells are used to drive the decoder/drivers 206. The outputs 242-245 of the control register cells are electrically connected to the appropriate digital inputs of the decoder/driver circuits 206 as shown in FIG. 4.

Figure 9A:
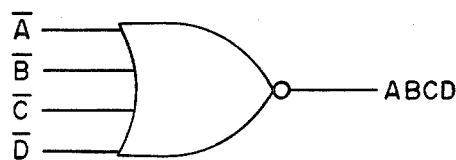
FIG. 9A is a logic diagram representing the circuits embodied in the decoder/driver blocks shown in FIG. 4.
Figure 9B:
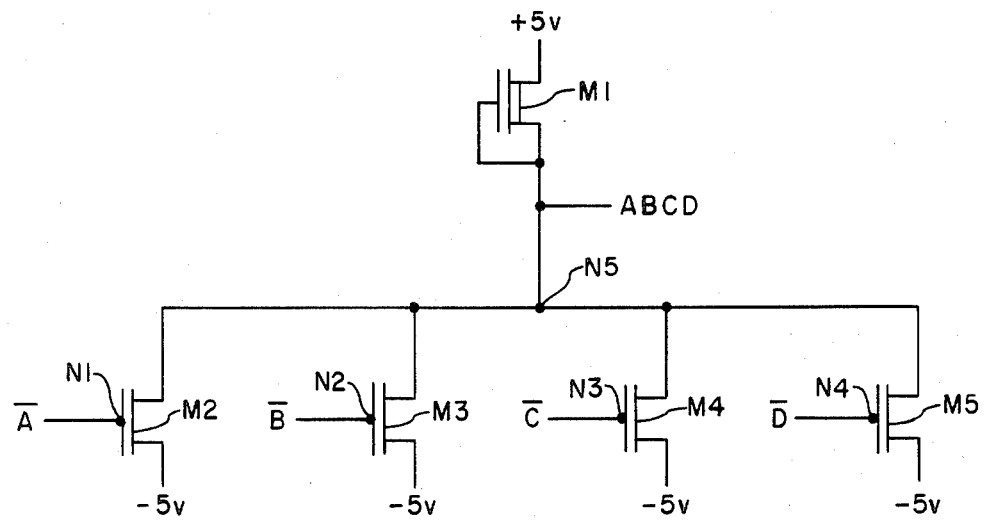
FIG. 9B is the schematic diagram of the circuit implementation of the logic diagram shown in FIG. 9A.

The decoder/driver circuits 206 each provide individual decoding using ten channels which are output at 232-241 (FIG. 4). FIG. 9A represents the logic diagram of the circuit for one channel. FIG. 9B shows the schematic diagram of the implementation of the logic diagram shown in FIG. 9A. For example, the channel corresponding to the circuit shown in FIGS. 9A and 9B will only be selected when all four shift register cell inverted outputs $\overline{A}$, $\overline{B}$, $\overline{C}$ and $\overline{D}$ are in a low state.

As indicated in the schematic in FIG. 9B, the gates of transistors M2 to M5 are individually connected to the shift register cell outputs $\overline{A}$-$\overline{D}$. The configuration of the circuit shown in FIG. 9B works so that if any shift register cell outputs $\overline{A}$-$\overline{D}$ enter a high state, one of transistors M2 through M5 will be turned on thus causing the voltage at node N5 to enter a low state, and it is this output which is applied to one of the analog multiplexors 206. Thus in the circuit shown in FIG. 9B, if any of the shift register cell inverted outputs $\overline{A}$-$\overline{D}$ are in a high state, that channel will not be selected.

By varying the connections of the true and inverted shift register cell outputs to M2 through M5 for each channel's circuit, various channels may be selected by altering the outputs of the control register cells. Thus, by use of a four bit word up to sixteen possible combinations of bit patterns may be selected.

The analog multiplexors 204 (FIG. 4) are common in the art. Each multiplexor 204 comprises ten pass transistors (not shown) which have their gates individually connected to the ten output channels 232-241 of the decoder/drivers 206. Each of the source terminals (not shown) of the ten pass transistors is individually connected to one of the ten analog inputs 227a-227h, 229a-229h, 228a-228b or 220a-220b of the analog multiplexors 204a or 204b. The source terminals of the pass transistors corresponding to eight of the channels of analog multiplexors 204 are individually connected to the outputs of the chemical sensors 100a-100h. The source terminal of the pass transistor for the remaining two channels are connected to ground 220 and to input 228 and the resistive voltage divider circuit 230-231. The purpose of the voltage divider circuit is to provide a predetermined voltage for testing the control circuitry of multiplexors 204.

The ten pass transistors (not shown) comprising each of the analog multiplexors 204 are such that the voltage present on the source terminal of each transistor is accurately reflected on the drain terminal of that transistor when the transistor is turned on, i.e., when that particular transistor has been selected by a decoder/driver 206. The drains of all ten pass transistors of each analog multiplexor 204 are connected. Thus, when any one of the ten pass transistors is turned on, or selected, the voltage present on the source of the particular pass transistor will appear at the parallel connection of all the drains of the pass transistors. The voltage output of the parallel drain connection is electrically connected to the outputs 202a-202b. By this configuration it is possible to route the output of any channel to one or both of the outputs 202a-202b on the integrated circuit 200.

Figure 10:
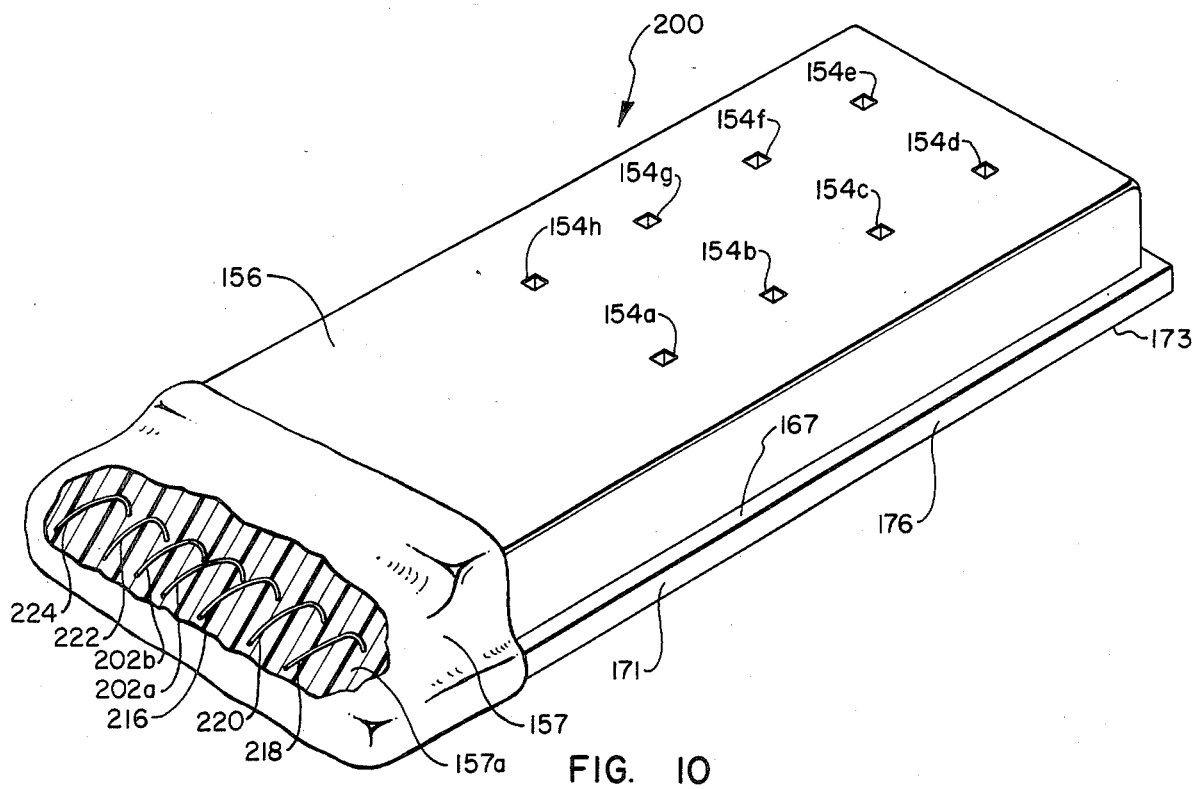
FIG. 10 is an enlarged perspective view of a completely fabricated integrated circuit of one presently preferred embodiment of the present invention.

FIG. 10 shows an enlarged perspective view of the completed integrated circuit 200 ready for use in chemical analysis. The chemical-selective membranes 108a-108h (see FIG. 3) are deposited and held in the membrane wells 154a-154h formed in the epoxy layer 156 directly over the metal input pads 158a-158h (shown in FIG. 3). By locating the membrane wells 154a-154h which have been formed in the layer 156 in this way, when the chemically selective membranes 108a-108h are placed in the membrane wells 154a-154h they will each contact the metal layer (shown in FIG. 3) and thus be electrically connected to the polysilicon gate 168 (also shown in FIG. 3) of the input transistor M1 (shown in FIG. 4) of amplifier 116. The shape and size of the membrane wells 154, as shown in FIG. 10, is merely representative and may be varied according to the type and size of chemical-selective membrane 108 to be placed in the well.

FIG. 10 also shows the seven bonded leads 202a-202b, 216, 218, 220, 222 and 224 which provide the external connections for the circuit 200, and which are also secured by an epoxy material 157. A portion of the epoxy material 157 is illustrated at 157a as being broken away to show the various leads. As mentioned above, the unencapsulated underside 173 of the substrate 176 is connected internally to a ground connection (see FIG. 3 at 169) so that the unencapsulated portion of substrate 176, which has a low resistance, can function as a solution contact for referencing the signal level of each chemical-sensor.

Because the reverse side 173 of substrate 176 can be used as a solution contact and because the circuit 200 is designed to be immersed in a fluid, it is important to chemically and electrically isolate the electronic circuitry of the integrated circuit 200 using the junction isolation layer 173, substrate 176 and the passivation layer 160 (see FIG. 3). The membrane definition layer 156, in addition to providing physical support for the chemical-selective membranes 108, must also provide electrical isolation between the individual membranes 108. The fabrication of the circuit so as to meet these requirements is discussed further in part III.

III. The Method of Fabrication

The integrated circuit for the chemical sensor of the present invention as described above could be fabricated using a variety of integrated circuit fabrication processes. Example 1 below illustrates one presently preferred method of fabrication that was used to produce prototype circuits of the type illustrated in FIG. 4. As mentioned previously, an important objective in the method of fabrication is simplification of the encapsulation process to eliminate tedious, time-consuming and irreproducible manual steps.

In the example, reference will be made to the following types of data:

1. The process run steps (Tables 1-10 contained in Appendix 3, incorporated herein by reference) and the drawings (FIGS. 11A-11K) representing the layout of each mask that is used in conjunction with the process run steps to form the various layers and circuit components on the semiconductor substrate.

2. SPICE simulation data (Appendix 1) comprising computer simulation of the design specifications and predicted performance of the particular semiconductor components. The input data for the SPICE simulation includes formation on the physical dimensions of the semiconductor devices formed on the substrate.

EXAMPLE 1

The concept of integrating a voltage-follower amplifier at each chemical-selective membrane site has led to the realization of an integrated eight-sensor transducer, the NP02, which can improve the accuracy of solid-state chemical monitoring. Not only does the NP02 multisensor provide the data required by chemical interference compensation algorithms, but the matched input transistors of individual sensors compensate for processing variations, aging and ambient changes to a degree never before attained by conventional sensors. The voltage-to-voltage transfer function permits use of any ion-selective membrane, facilitates high-speed multiplexing and provides a simpler mathematical model. On-chip feedback improves input and output impedances and transfer function stability by more than three orders of magnitude. Importantly, use of silicon-gate input transistors, as opposed to membranes applied directly over the gate oxide as in the case of prior art CHEMFET devices, de-couples effects of the electrochemical measurement function from the sensing circuitry.

The NP02 multisensor integrated circuit was designed on a Computervision CGP-100 design system, using the computer-aided design program CADDS 2/VLSI. Layouts for the various masks shown in FIGS. 11A-11K and in appendix 2 were produced with these computer-aided design tools, and plotted on a Calcomp 960 plotter.

Photographic images (10X) were generated on a David Mann 2600 pattern generator. These patterns were mounted on master frames using a David Mann 3319 high-precision master reticle alignment instrument; and the image was reduced to true size and replicated to make the working masks of FIGS. 11A-11K in a David Mann 3095 step-and-repeat camera.

The NP02 multisensor integrated circuit was designed in accordance with the embodiment of the present invention of FIGS. 4 and 10. First, wafers were obtained having an epitaxial layer of a p-type silicon (see FIG. 3 at 174) grown on an n-type silicon substrate (FIG. 3 at 176). Upon the epitaxial layer a mask oxide layer (not shown) was thermally grown, which was later stripped. The mask oxide layer was patterned using mask 9 (FIG. 11A) so as to open the mask oxide along scribe lanes formed between individual chips on the wafer. Phosphorus was diffused into the exposed scribe lanes using a pattern 1¾ mils wider than each side of the scribe lanes. This formed the junction isolation layer (see FIG. 3 at 173) of n-type silicon around the entire periphery of the integrated circuit. Table 1 describes the process run steps 1-9 used to develop the junction isolation layer.

Since the substrate and junction isolation layer are both n-type silicon whereas the epitaxial layer is p-type silicon, the substrate and isolation layers form diode junctions at the interfaces (173 and 177 of FIG. 3) with the epitaxial layer. The epitaxial layer is typically connected to the negative source voltage ($-5$ v), and the isolation layer and substrate are connected to ground. As described above, this permits the isolation layer and substrate to serve as solution contacts for purposes of providing a reference voltage, and provides the further advantage that the edges and reverse side of each chip need not be hand-encapsulated.

Figure 11A:
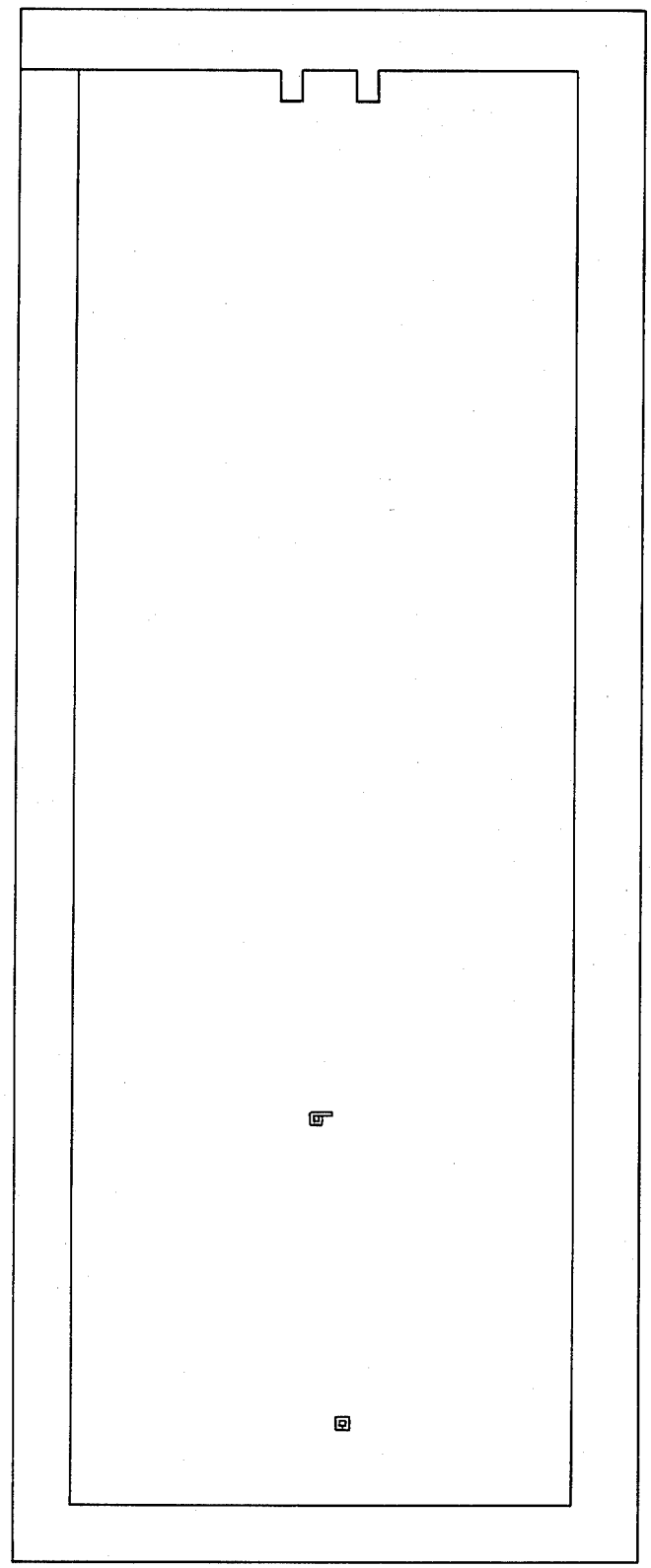
Figure 11B:
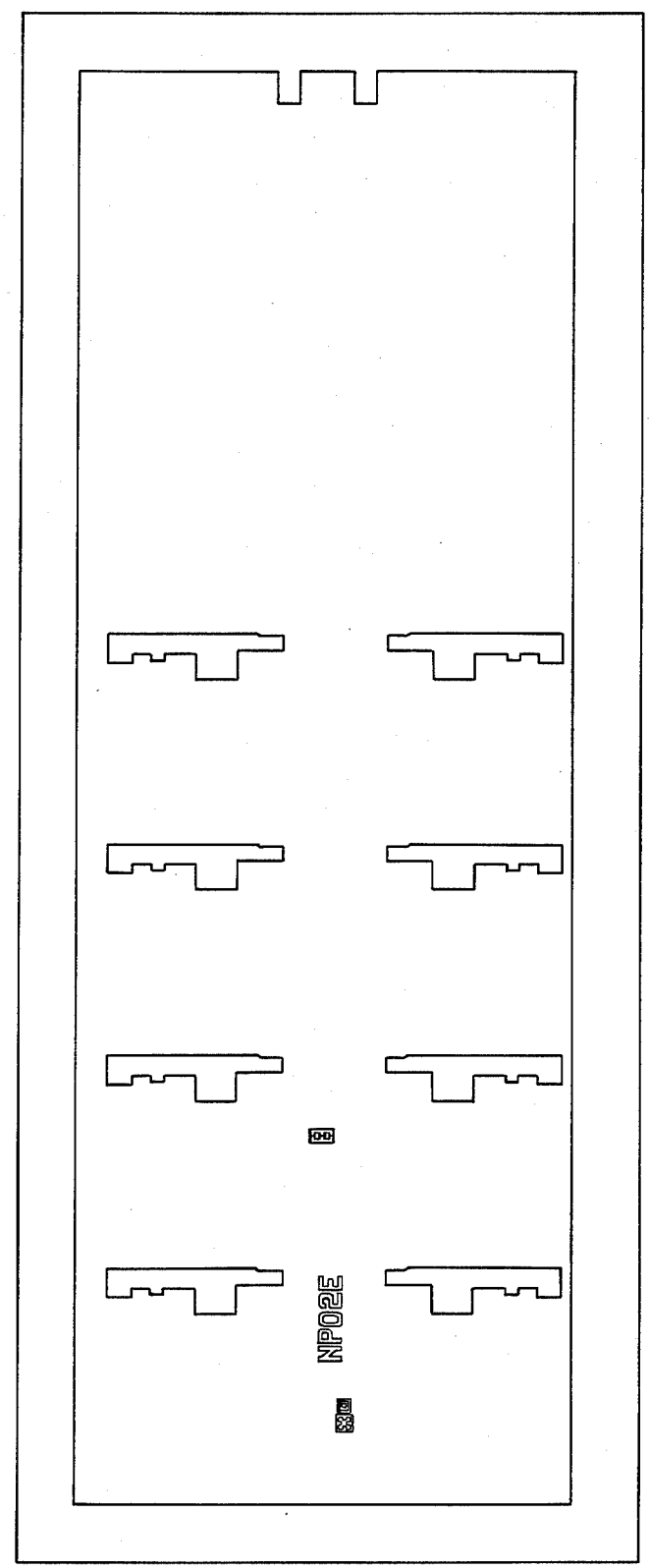
Figure 11C:
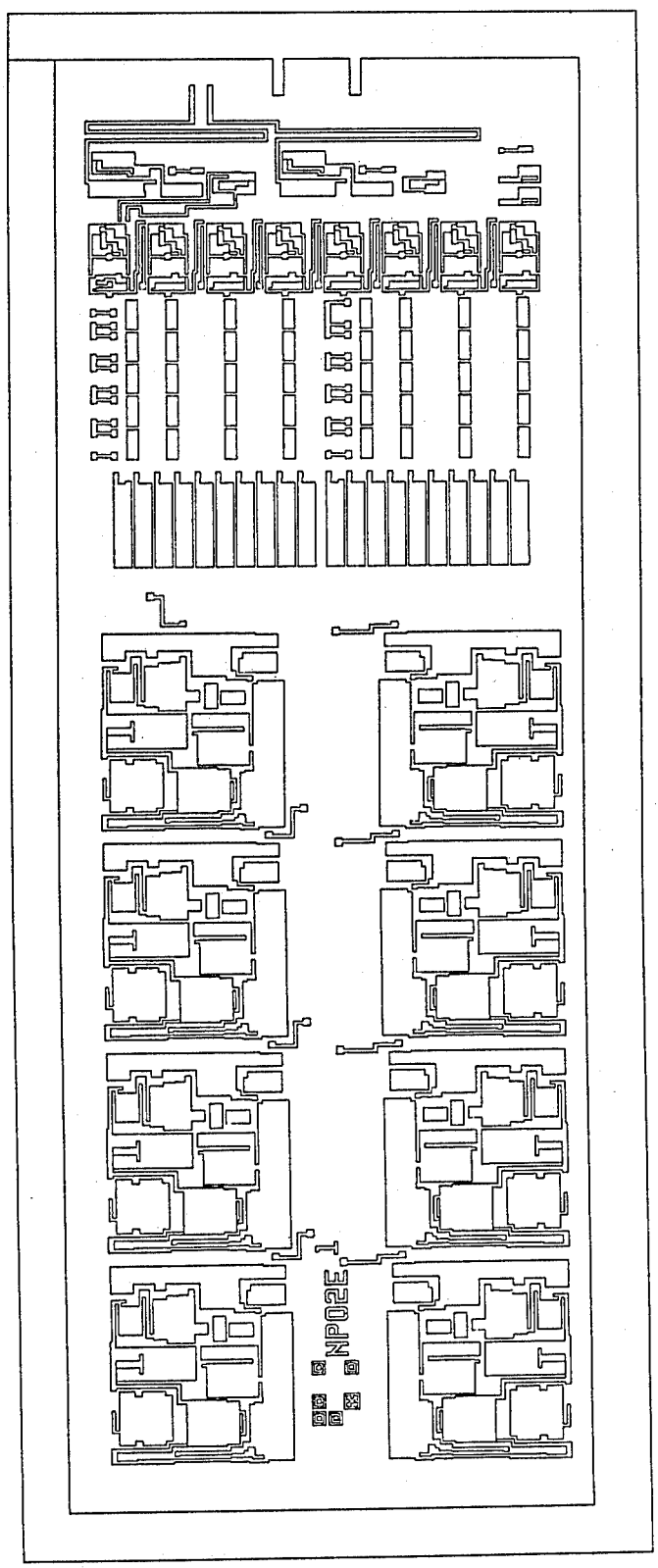

Next, the bottom plates of thin oxide capacitors were formed using mask layout 8 as illustrated in FIG. 11B. The process run steps 10-17 set forth in Table 2 were used in connection with mask layout 8 to define the capacitor regions and to diffuse the capacitor plates. Mask layout 1 as shown in FIG. 11C was then used in accordance with the process run steps 18-33 as set forth in Table 3 to differentiate the active area (see, for example, 170s, 170c and 170d of FIG. 3) from the field oxide area (172 of FIG. 3). A gate oxide layer (see 169 of FIG. 3) was then grown over the channel area (FIG. 3 at 170c). The channel area was differentiated from the source and drain areas by mask 4, described below.

Figure 11D:
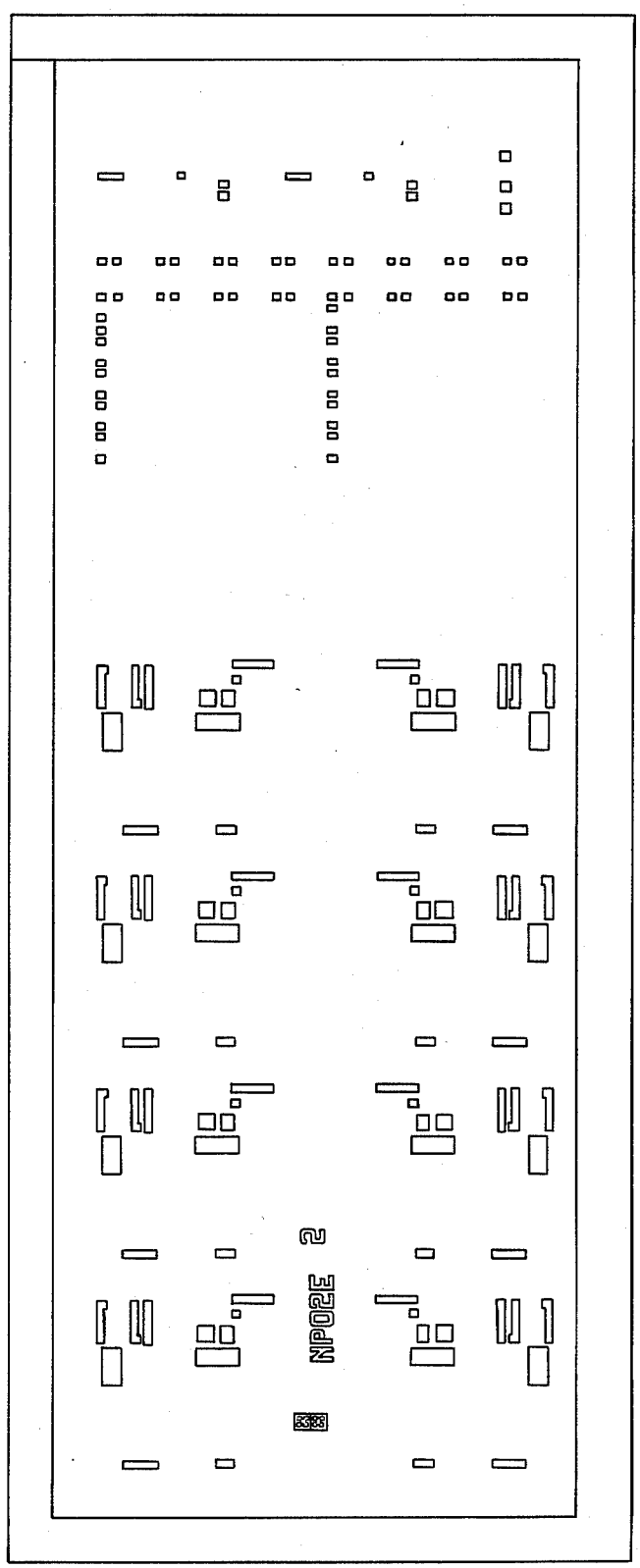
Figure 11E:
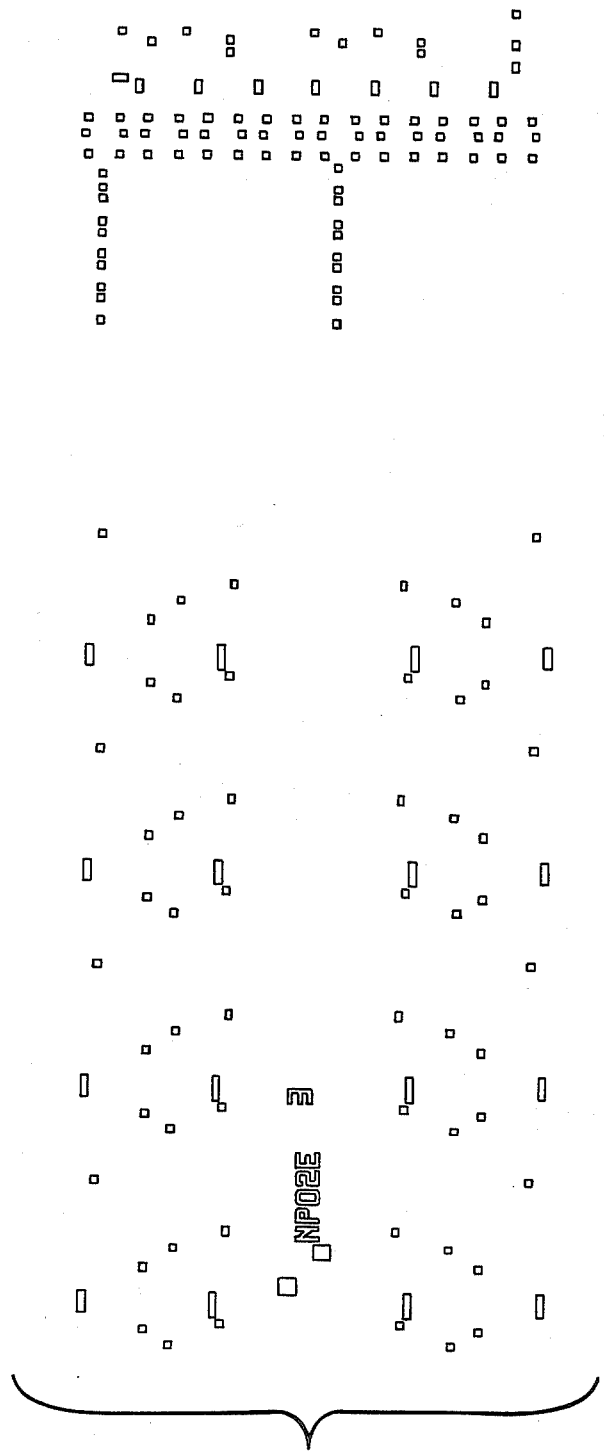
Figure 11F:
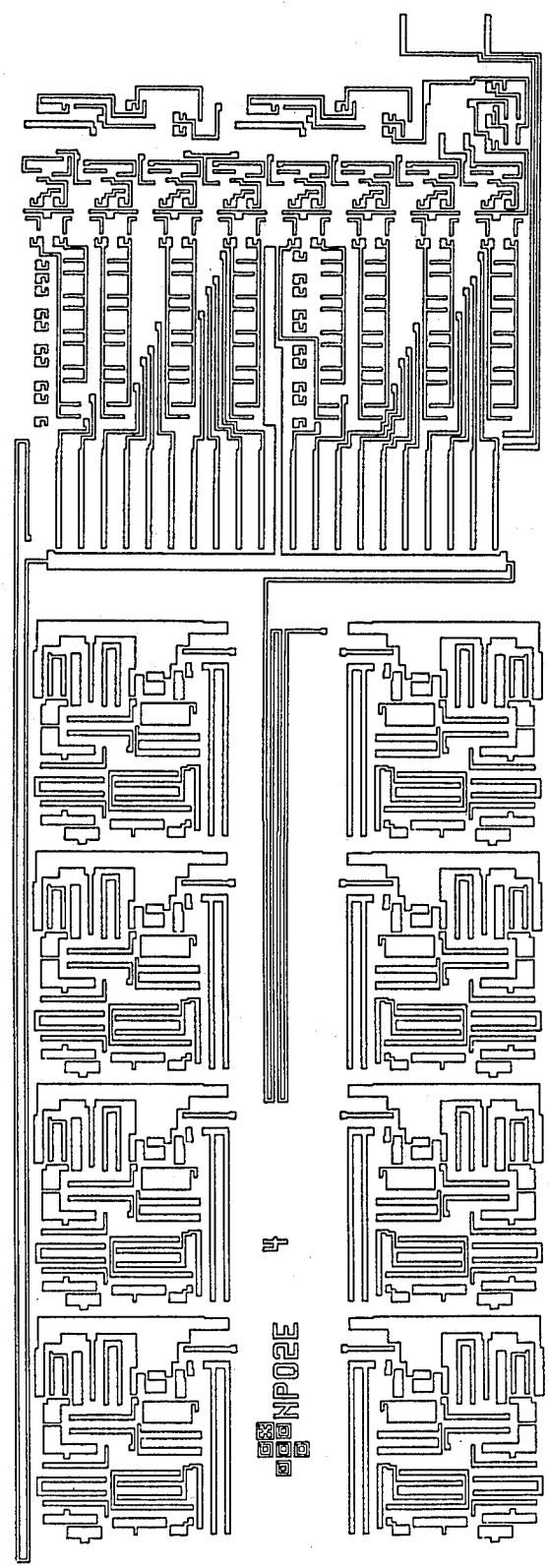
Figure 11H:
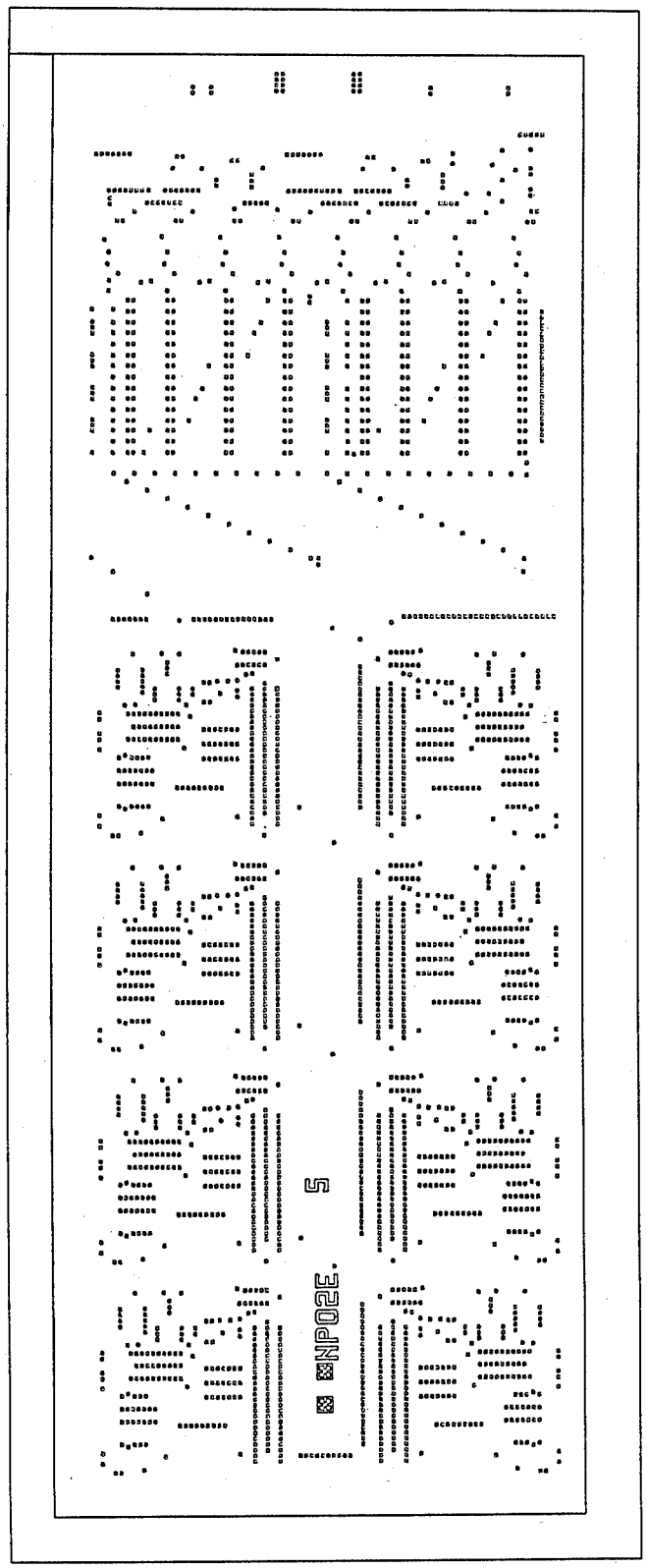

Next, mask layout 2 as shown in FIG. 11D was used in conjunction with steps 34-37 of Table 4. During these steps, boron was implanted into selective transistors to make depletion devices, as identified in Appendix 1. Mask layout 3 illustrated in FIG. 11E was then used according to process run steps 38-43 (Table 5) to form openings for each of the contacts needed between the next layer, polysilicon, and diffused conductors. A layer of polysilicon (see FIG. 3 at 168) was then deposited and patterned using mask layout 4 (FIG. 11F) in conjunction with process run steps 44-52 of Table 6. The polysilicon was doped to render it conducting, the drains and sources were doped, and the back of the wafer was doped for gettering in a single phosphorus deposition. Process step 53 (Table 6) was then used to deposit another layer of silicon dioxide insulator (FIG. 3 at 164), and process step 54 (Table 6) was used to create physical damage gettering on the backside of the wafer.

Process run steps 56-69 of Table 7 and mask layout 10 (FIG. 11G) were then used to partially open contact holes for top-side metal contact to the epitaxial layer. Steps 60-62 were used with mask layout 5 (FIG. 11H) to complete the contact holes to the epitaxial layer and to open contacts for metal to both silicon and diffusions.

A metal layer (see FIG. 3 at 162) was then deposited upon the pyro oxide layer and patterned using mask layout 6 of FIG. 11I and process run steps 63-68 (Tables 8 and 9). A passivation layer (see FIG. 3 at 160) was then deposited upon the entire surface and openings were formed in the passivation layer (see FIG. 3 at 159) at each point where a chemical-selective membrane was to be in contact with the metal layer. The passivation layer was formed using step 69 at Table 10. The openings formed in the passivation layer were produced using mask layout 7 of FIG. 11J and process run steps 70-72 of Table 10.

A membrane definition layer (see FIG. 3 at 156) was prepared by coating the completed integrated circuit with a 100-micron thick layer of RISTON®, an adaptable photosensitive emulsion which is commercially available from E. I. DuPont Company. The RISTON® emulsion was patterned using the mask layout 14 shown in FIG. 11K. Using the mask layout 14, chimneys were formed by etching away the RISTON® (which is photosensitive) so as to remove the RISTON everywhere except where the chimneys are desired (i.e., everywhere except over scribe lanes, bonding pads and input pads). The multisensor integrated circuit was then coated with epoxy and the epoxy was lapped down to the RISTON®, and the remaining RISTON® was then stripped. With the RISTON® removed, the epoxy was left with wells into which the membranes were then deposited.

The membrane wells may be formed as squares having sides as small as 1.0 mil. Larger wells could be formed using, for example, a mask layout such as mask layout 17 of FIG. 11L. Mask layout 17 provides chimneys which, when removed will leave a square well with a side of 15.0 mil. The larger wells are intended to be used with conventional, solvent-cast polymeric membranes whereas the smaller wells are designed for holding liquid ion exchangers in place with surface tension.

With the membrane wells formed, chemical-selective membranes for potassium (K+), calcium (Ca++), sodium (Na+) and pH were applied to the membrane wells. Various combinations of the chemical-selective membranes of each indicated type were used. The compositions of each membrane material which were used are set forth in Table 11.

The membranes were cast by dissolving the ionophore/PVC mixtures shown in Table 11 in cyclohexanone, depositing a small amount of this in the membrane well and allowing it to dry 10 to 30 minutes. This procedure was repeated four or five times to eliminate pinholes, and to form a membrane about 100 microns thick. The membranes were dried in a desiccator at room temperature and atmospheric pressure for two or more days.

Importantly, the above-described technique for encapsulating the integrated circuit and preparing the membrane definition layer are advantageous because they accommodate mass production using a planar process rather then relying on difficult and time-consuming manual operations. The nitride passivation layer (FIG. 3 at 160) provides an hermetic seal between the active circuit areas of the integrated circuit and the metal contact surface of the chemical-selective membrane to prevent contamination of the contact surface by the fluid being analyzed. The membrane definition layer provides electrical isolation between the different chemical-selective membranes. Other techniques could be used to form encapsulation and membrane definition layers having these characteristics.

Figure 11L:
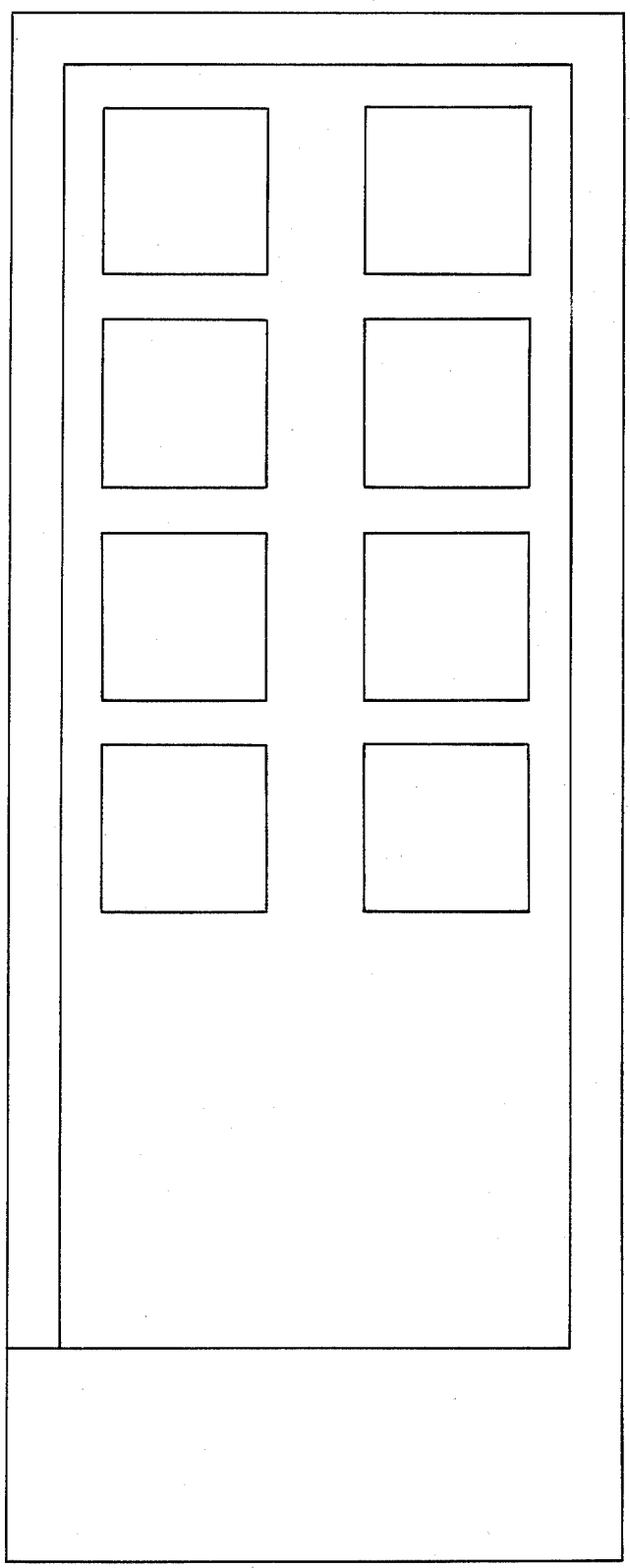

For example, another method which may be used to form the membrane definition layer requires that epoxy be directly spun onto the finished surface of the entire integrated circuit. The epoxy layer is then coated with a mask layer of aluminum or polysilicon. The mask layer of aluminum or polysilicon is patterned using masks such as shown in FIGS. 11K-11L, and the epoxy layer is etched to form the membrane wells.

Still another method available to form the membrane definition layer uses a dry film acrylic photopolymer, such as VACREL®, also a commercial product of E. I. DuPont Company. Since VACREL® is photosensitive it is applied directly to the finished surface and directly patterned using a mask layout such as those in FIGS. 11K-11L. The VACREL® is chemically developed and then cured to form a hard, hydrophobic membrane definition layer.

Another method which may be used to form the membrane definition layer involves spinning a layer of polyimide directly onto the finished wafers. The polyimide is then patterned with a photoresist, since polyimide is not photosensitive. The photoresist is patterned using a mask layout such as that found in FIGS. 11K-11L. The polyimide is then etched and the mask layer stripped from the finished encapsulated integrated circuit leaving the membrane wells in the membrane definition layer. After formation of the membrane definition layer by any of the methods outlined above, the chemical-selective membranes are placed in the membrane wells as previously described.

The dimensions of the various circuit components used to form the NP02 multisensor as well as the predicted performance characteristics are set forth in the SPICE simulation data of Appendix 1 hereto, which is incorporated herein by reference. The circuit design rules which were used with the various mask layouts of FIGS. 11A-11K are set forth in Table 12.

Appendix 2, incorporated herein by reference, contains the computer-generated color drawings showing the mask overlays 1-10 in an aligned, composite drawing for the overall NP02 multisensor integrated circuit, including each of the major blocks of the NP02 as schematically shown in FIG. 4. The mask overlays 1-10 are color coded in the drawings of Appendix 2 as follows: green—masks 1, 8 and 9; orange—mask 2; brown—mask 3; red—mask 4; cyan—mask 5; blue—mask 6; magenta—mask 7; and black—mask 10.

I claim:

1. An integrated circuit for a miniaturized solid-state chemical sensor, said integrated circuit comprising:
   a semiconductor substrate;
   a plurality of layers formed on said substrate so as to define a plurality of transistors configured as an amplifier, two of said transistors comprising field-effect input transistors with essentially identical dimensions and gate electrodes;
   a chemical-selective membrane;
   a membrane definition layer applied over said layers defining said amplifier, said membrane definition layer comprising a well for receiving said chemical-selective membrane, said well being formed in sufficient proximity to said gate electrode of at least one of said input transistors such that said chemical-selective membrane is separated from said gate electrode by no greater distance than the largest dimension of said input transistors;
   means formed on said substrate for electrically connecting said chemical-selective membrane to said gate electrode of one of said input transistors; and
   said gate electrode of said other input transistor being electrically connected to said output of said amplifier to provide a unity-gain buffer.

2. An integrated circuit as defined in claim 1 wherein said means formed on said substrate for electrically connecting said chemical-selective membrane to said gate material of one of said input transistors comprises a metal layer interposed between said membrane definition layer and said layers forming said transistors.

3. An integrated circuit as defined in claim 2 wherein said metal layer comprises a first contact location electrically connected to said chemical-selective membrane and a second contact location electrically connected to said gate electrode of one of said input transistors.

4. An integrated circuit as defined in claim 3 wherein said means formed on said substrate for electrically connecting said chemical-selective membrane to said gate electrode of one of said input transistors further comprises a passivation layer formed over said metal layer and having an opening formed therein so as to define said first contact location on said metal layer, and further comprising an insulating layer formed under said metal layer and having an opening formed therein so as to define said second contact location.

5. An integrated circuit as defined in claim 3 wherein said membrane definition layer comprises a well formed in said membrane definition layer over said first contact location, and wherein said chemical-selective membrane is deposited in said well so as to electrically contact said metal layer at said first contact location.

6. An integrated circuit as defined in claim 5 wherein said membrane definition layer is completely formed by a planar process.

7. An integrated circuit as defined in claim 6 wherein said planar process comprises the steps of:
   coating the top of said integrated circuit with a layer of a photosensitive emulsion;
   patterning said layer of photosensitive emulsion with a mask and etching said emulsion so as to leave a chimney defined by said mask at the place where said well is to be formed;
   coating the surface of said integrated circuit with a layer of epoxy and lapping said epoxy down to the level of said chimney; and
   stripping said emulsion forming said chimney so as to leave said well in said layer of epoxy.

8. An integrated circuit as defined in claim 6 wherein said planar process comprises the steps of:
   spinning a layer of epoxy onto the top of said integrated circuit;
   coating said layer of epoxy with a layer of material from the group of materials consisting of aluminum and polysilicon;

patterning said layer of material with a mask to defined the location at which said well is to be formed; and etching said layer of epoxy to form said well at said location.

9. An integrated circuit as defined in claim 6 wherein said planar process comprises the steps of:
coating the top of said integrated circuit with a layer of dry film acrylic photopolymer;
patterning said layer of photopolymer with a mask layout to define said well; and
curing said layer of photopolymer.

10. An integrated circuit as defined in claim 6 wherein said planar process comprises the steps of:
spinning a layer of polyimide onto the top of said integrated circuit;
coating said layer of polimide with a photoresist;
patterning said photoresit with a mask layout to define the location at which said well is to be formed; and
etching said layer of polyimide to form said well at said location, and stripping away said photoresist.

11. An integrated circuit as defined in claim 5 wherein said chemical-selective membrane comprises a liquid ion exchanger and wherein the size of said well is selected such that said liquid is held in said well by surface tension.

12. An integrated circuit as defined in claim 5 wherein said chemical-selective membrane comprises a solvent-cast polymeric membrane.

13. An integrated circuit as defined in claim 1 wherein said transistors are connected to form a plurality of voltage-follower amplifiers, each said amplifier comprising a pair of field-effect input transistors having essentially identical dimensions and gate electrodes.

14. An integrated circuit as defined in claim 13 further comprising a plurality of chemical-selective membranes held by said membrane definition layer, and wherein said means formed on said substrate comprises means for electrically connecting each said membrane to said gate electrode of one of said pair of input transistors of a corresponding amplifier for said membrane.

15. An integrated circuit as defined in claim 14 wherein one or more of said membranes are adapted to sense a different chemical than the chemical sensed by the other said membranes.

16. An integrated circuit as defined in claim 14 further comprising means for outputting an electrical signal from at least one of said amplifiers, and means for selectively switching from one of said amplifiers to another so as to be able to selectively connect an output voltage from any said amplifier to said means for outputting said electrical signal.

17. An integrated circuit for a miniaturized solid-state chemical sensor adapted to sense one or more selected chemicals in a fluid, said integrated circuit comprising:
a semiconductor substrate;
a plurality of layers formed on said substrate so as to define a plurality of transistors interconnected to form a plurality of voltage-follower amplifiers, each said amplifier comprising a pair of field-effect input transistors having essentially identical dimensions and gate electrodes;
a membrane definition layer applied over said layers defining said amplifiers;
a plurality of chemical-selective membranes held by said membrane definition layer, each said membrane being secured to a region of said membrane definition layer so as to be essentially immediately adjacent the gate electrode of a corresponding input transistor;
a metal layer formed between said membrane definition layer and said plurality of layers defining said transistors, said metal layer comprising a series of electrical contact locations providing electrical contact between each said chemical-selective membrane and the gate electrode of one of said input transistors of a corresponding amplifier for said chemical-selective membrane; and
said plurality of layers further defining means formed on said substrate for outputting an electrical signal from at least one of said amplifiers, and means for selectively switching from one of said amplifiers to another so as to be able to selectively connect an output voltage from any said amplifier to said means for outputting said electrical signal.

18. An integrated circuit as defined in claim 17 wherein one or more of said chemical-selective membranes are adapted to sense a different chemical than the chemical sensed by the other said membranes.

19. An integrated circuit as defined in claim 17 wherein said membrane definition layer is completely formed by a planar surface.

20. An integrated circuit as defined in claim 19 wherein said planar process comprises the steps of:
coating the top of said integrated circuit with a layer of a photosensitive emulsion;
patterning said layer of photosensitive emulsion with a mask and etching said emulsion so as to leave a chimney defined by said mask at the place where said well is to be formed;
coating the surface of said integrated circuit with a layer of epoxy and lapping said epoxy down to the level of said chimney; and
stripping said emulsion forming said chimney so as to leave said well in said layer of epoxy.

21. An integrated circuit as defined in claim 19 wherein said planar process comprises the steps of:
spinning a layer of epoxy onto the top of said integrated circuit;
coating said layer of epoxy with a layer of material from the group of materials consisting of aluminum and polysilicon;
patterning said layer of material with a mask to define the location at which said well is to be formed; and
etching said layer of epoxy to form said well at said location.

22. An integrated circuit as defined in claim 19 wherein said planar process comprises the steps of:
coating the top of said integrated circuit with a layer of dry film acrylic photopolymer;
patterning said layer of photopolymer with a mask layout to define said well; and
curing said layer of photopolymer.

23. An integrated circuit as defined in claim 19 wherein said planar process comprises the steps of:
spinning a layer of polyimide onto the top of said integrated circuit;
coating said layer of poylimide with a photoresist;
patterning said photoresist with a mask layout to define the location at which said well is to be formed; and
etching said layer of polyimide to form said well at said location, and stripping away said photoresist.

24. An integrated circuit as defined in claim 17 wherein at least one of said chemical-selective membranes comprises a liquid ion exchanger.

25. An integrated circuit as defined in claim 17 wherein at least one of said chemical-selective membranes comprises a solvent-cast polymeric membrane.

26. An integrated circuit as defined in claim 17 further comprising a junction isolation layer formed around the entire periphery of said layers forming said transistors so as to extend to and slightly under the edges of said layers forming said transistors.

27. An integrated circuit as defined in claim 26 wherein said passivation layer overlaps the edges of said junction isolation layer, and wherein said layers forming said transistors are chemically and electrically isolated from said fluid by the combination of said substrate, said junction isolation layer and said passivation layer.

28. An integrated circuit as defined in claim 27 further comprising means for providing an internal ground connection, and wherein said substrate and said junction isolation layer are electrically connected to said internal ground connection so as to form a solution contact for referencing an output voltage of each said amplifier.

* * * * *

UNITED STATES PATENT AND TRADEMARK OFFICE
CERTIFICATE OF CORRECTION

PATENT NO. : 4,743,954

DATED : May 10, 1988

INVENTOR(S) : Richard B. Brown

It is certified that error appears in the above-identified patent and that said Letters Patent is hereby corrected as shown below:

Column 18, line 41, "formation" should be --information--
Column 20, lines 13-14, "(Tables (8 and 9)" should be --(Tables 8 and 9)--
Column 23, lines 1-2, "to defined" should be --to define--
Column 24, line 63, "poylimide" should be -- polyimide --.

Signed and Sealed this

Thirteenth Day of February, 1990

Attest:

JEFFREY M. SAMUELS

*Attesting Officer*   *Acting Commissioner of Patents and Trademarks*